United States Patent [19]

Nakane et al.

[11] Patent Number: 5,122,418
[45] Date of Patent: Jun. 16, 1992

[54] COMPOSITE POWDER AND PRODUCTION PROCESS

[75] Inventors: Toshihiko Nakane, Yokohama; Masumi Koishi, Sagamihara; Hiroshi Fukui, Yokohama; Yutaka Okunuki, Yokohama; Yoshio Yahata, Yokohama; Shigenori Kumagai, Yokohama; Hiroyuki Yokoyama, Yokohama; Eiichiro Yagi, Yokohama; Minoru Fukuda, Yokohama; Tadao Ohta, Yokohama; Fujihiro Kanda, Yokohama; Kazuhisa Ohno, Yokohama; Toshihide Ebisawa, Yokohama; Tomiyuki Nanba, Yokohama; Susumu Takada, Yokohama; Masato Hatao, Yokohama; Masaru Suetsugu, Yokohama, all of Japan

[73] Assignee: Shiseido Company Ltd., Tokyo, Japan

[21] Appl. No.: 593,537

[22] Filed: Oct. 4, 1990

Related U.S. Application Data

[63] Continuation of Ser. No. 405,702, Sep. 11, 1989, abandoned, which is a continuation of Ser. No. 375,616, May 24, 1989, abandoned, which is a continuation of Ser. No. 939,379, Dec. 8, 1986, abandoned.

[30] Foreign Application Priority Data

Dec. 9, 1985 [JP] Japan .................. 60-276505
Jul. 22, 1986 [JP] Japan .................. 61-172499
Nov. 21, 1986 [JP] Japan .................. 61-278374

[51] Int. Cl.$^5$ ............................................. A61K 6/00
[52] U.S. Cl. ................................ 424/401; 424/59; 424/76.2; 424/76.25; 424/489; 424/46; 424/47
[58] Field of Search ............... 424/489, 501, 471, 59, 424/76.2, 76.25, 46, 47

[56] References Cited

U.S. PATENT DOCUMENTS 4,537,913  8/1985  Bauman .................. 528/260
4,669,492  6/1987  Kleinsorgen ............. 424/DIG. 5.4

FOREIGN PATENT DOCUMENTS 53-13626  2/1978  Japan .
57-81823  5/1982  Japan .

OTHER PUBLICATIONS

C.A. vol. 89, 94884d, 1978, p. 382 "Powders-Porous Powders for Cosmetics"; JP7813626.
C.A. vol. 97, 150585m, 1982 "Porous Powder for Skin Cosmetics", JP8686,823.

Primary Examiner—Thurman K. Page
Assistant Examiner—Leon R. Horne
Attorney, Agent, or Firm—Sprung Horn Kramer & Woods

[57] ABSTRACT

A composite powder wherein an organic or inorganic core powder is substantially completely covered with one or more types of organic, inorganic, or metallic powders having an average particle size one-fifth or less of the average particle size of the above core powder by means of mixing and compression. The composite powder may be manufactured by mixing and compressing the above core powder and coating powder using a ball mill or other mixer charged with a ball shaped mixing medium of an average diameter of 5 mm or less. This composite powder may be used in, for example, skin treatment agent, makeup type cosmetics, sunburn preventing cosmetics, deodorants.

5 Claims, 5 Drawing Sheets

COMPOSITE POWDER AND PRODUCTION PROCESS

This application is a continuation, of U.S. Ser. No. 405,702 filed Sep. 11, 1989, now abandoned, which is a continuation of application Ser. No. 375,616, filed May 24, 1989, now abandoned, which was a continuation of U.S. application Ser. No. 06/939,379, filed Dec. 8, 1986, now abandoned.

BACKGROUND OF THE INVENTION

1. Field of the Invention

The present invention relates to a composite powder wherein the surface of one type of core powder is substantially completely covered with another type of coating powder, thereby improving the surface characteristics of the powder, and a production process and use thereof. More particularly, it relates to a composite powder with a core powder substantially completely covered with a coating powder, and a production process thereof, and a skin treatment agent containing the same, wherein use is made of a ball mill or other continuous or noncontinuous type mixer charged with a ball-shaped mixing medium with ah average diameter of 5 mm or less for mixture and compression, one type of organic or inorganic powder being used as the core powder and an organic, inorganic, or metallic powder with an average particle size of one-fifth or less of the average particle size of the core powder being used as the coating powder.

Note that in this specification, "substantially completely covered" means a state wherein the core powder is homogeneously and closely covered by the coating powder. However, when microscopically examining the composite powder formed by substantially completely covering the core powder with the coating powder, it will be seen that there are extremely narrow gaps between the particles of the coating powder.

Further, in this specification, "spherical powder" means any powder from a true spherical shape to an ovoid shape with a long diameter to short diameter ratio of 2:1, and includes slightly deformed powder also.

2. Description of the Related Art

In the prior art, use has been made of ball mills, automated mortars, automatic mortars, and the like to mix and pulverize nylon powder, polymethylmetacrylate powder, and other types of plastic powder and organic powders, titanium dioxide, red oxide, and other inorganic powders by the wet or dry method so as to produce composite powder. However, in the above methods used in the prior art, there are many unsolved problems, such as nonuniformity of the coating, deformation of the core powder, and separation of the coating powder, which detract from the stability of the composite powder.

Conventional cosmetics for use in treating rough skin are prepared with due consideration to the components contained in the secretions of the skin and the components contained in the skin so as to assist the action of the skin by adding moisture retaining components or oils and supplementing components in the skin, thereby maintaining the skin in its normal state or improving it. Further, medicines with an antioxidation function have been added to reduce the products of decomposition of sebum which have a detrimental effect on the skin. However, these effects are still unsatisfactory. Among the skin treatment agents, there are those including medicines with a skin activation or skin inflammation suppression effect, but stabilization of these is difficult and there are limits to the amount of such medicines which can be compounded.

The inventors engaged in in-depth research for an effective method of maintaining the skin in its normal state and preventing or improving rough skin. As a result, they discovered that it was effective to remove from the sebum components the old waste products of the skin, which have a detrimental effect on the skin. For this purpose, they found that hydroxyapatite powder was superior in selective adsorption of the old waste products of sebum, i.e., free fatty acids and liquid peroxide, and was effective for the prevention of rough skin, improving rough skin, and suppression of skin inflammation of patients suffering from acne. However, if hydroxyapatite powder is compounded in a skin treatment agent as it is, the hydroxyapatite powder would not sufficiently spread over the skin since it has a strong agglomeration property, so the problem remained that the full effect of the adsorption of the decomposed sebum could not be enjoyed.

On the other hand, makeup type cosmetics are usually produced with the inclusion of some oils, wax, hydrocarbons, higher alcohols, and other oil components, powders, coloring matter, and other components, e.g., antioxidants, plasticizers, and solvents. Such makeup type cosmetics have been given a better feel, i.e., a better smoothness and easier applicability, by the addition of spherical powder. However, polyamide resin, polyethylene resin, methyl methacrylate resin, cellulose resin, polystyrene resin, polypropylene resin, styrene and acrylate copolymers, and other organic spherical powder, silica, alumina, magnesium carbonate, and other inorganic spherical powder can impart to makeup type cosmetics the desired feel, i.e., excellent smoothness and easy applicability, because the particles thereof are spherical in shape, but the spherical powders have a low index of refraction, so are poor in hiding power. Therefore, if these spherical powders are compounded in makeup type cosmetics such as foundations, in which a high hiding power is sought, the desired hiding power will not be imparted. When a powder with a high index of refraction is used at the same time to impart the hiding power, a uniform skin covering effect cannot be obtained due to the large difference in hiding powers. This leads to streaking and blotching and thus detracts considerably from the beauty of the finish when applying foundation to the skin. Further, the afore-mentioned spherical powder is a low refractive index powder, and when used together with coloring agents, the problems arise of uneven color, color separation, and color streaking and blotching, from which point also there is a significant detraction from the stability of the product and the beauty of the finish upon application. The same problems of uneven color, color separation, and color streaking and blotching occur in compounding a spherical powder having a high index of refraction, such as titanium dioxide.

Further, it is known in the art to use a ball mill, automated mortar, automatic mortar, etc. to mix and pulverize, by the wet method or dry method, spherical nylon powder, spherical polymethylmetacrylate powder, and titanium dioxide, red iron oxide, and other inorganic powders to produce a composite powder, but the prior art products have featured a nonuniform covering of the coating powder, i.e., not a substantially complete covering, and a slight mechanical force was sufficient to cause an easy separation of the coating powder. The coating powder would also separate easily in oils or solvents. Thus, the problem remains that the stability of the composite powder is not sufficient. Composite powders suffering from such problems have the disadvantage that, due to the nonuniformity of the covering of the coating powder on the spherical core powder, first, the shape of the powder becomes significantly different from the spherical shape, so the powder cannot impart an excellent smoothness and easy applicability to makeup type cosmetics. Second, when a spherical powder having a low index of refraction is covered with a white coating powder, portions with no hiding power are exposed, and thus the hiding power given to the makeup type cosmetic is insufficient or differences in the hiding power arise, leading to streaks and blotching and significantly detracting from the beauty of the finish upon application to the skin. Also, when the coating powder is a colored powder, uncolored portions are exposed, leading to uneven color, color separation, and color streaking and blotches, similarly significantly detracting from the beauty of the finish. Third, even when a high index of refraction spherical powder is covered with a colored powder, similar problems arise as when covering a low index of refraction spherical powder by a colored powder.

Note, it is known that the ultraviolet rays in sunlight causes acute inflammation of the skin upon overexposure to the same, and long-term exposure causes early aging of the skin, pigmentation, and wrinkles and is a factor behind skin cancer. Therefore, as the effects of ultraviolet rays on the skin have become clearer, the demand for sunburn preventing cosmetics which protect the skin from ultraviolet rays has been rising.

Sunburn preventing cosmetics contain ultraviolet absorbents or ultraviolet scatterers for blocking the ultraviolet rays. Known ultraviolet absorbents include benzophenones, cinnamic acids, benzoic acids, etc. These have a narrow ultraviolet absorption band in most cases and cannot necessarily be said to have a satisfactory blockage of a wide range of ultraviolet rays. Also, they interact with the other components of the cosmetic, and thus degrade the stability of the product or, when a larger amount is compounded so as to raise the ultraviolet absorption effect, cause problems in terms of skin safety. Therefore, to block a wide range of ultraviolet rays, use is made of ultraviolet scatterers. As ultraviolet scatterers, use is made of zinc oxide, titanium oxide, kaolinite, calcium carbonate, and other inorganic pigments. However, while inorganic pigments displaying such ultraviolet scattering effects have a high skin safety and effectively scatter a wide spectrum of ultraviolet rays, when compounded in cosmetics, they enter into an agglomerated state known as secondary agglomeration, and thus a large amount must be compounded to give a sufficient ultraviolet scattering effect. In such a case, the hiding power becomes too great, and thus, when the cosmetic is applied to the skin, it appears too heavy, resulting in the problem of an unnatural finish. A similar art to the present invention is Japanese Unexamined Patent Publication (Kokai) No. 61-194013, entitled "Sunburn Preventing Cosmetic". In that publication, disclosure is made of the use of particles of an insoluble polymer compound to which titanium oxide is adhered. The covering power of the titanium oxide is too high, however, and has a hiding power six to seven times that of zinc oxide. Therefore, when compounded with the aim of raising the ultraviolet scattering effect, the result is again a too heavy makeup appearance.

Further, in Japanese Unexamined Patent Publication (Kokai) No. 60-231607, entitled "Sunburn Preventing Cosmetic", disclosure is made of compounding zinc oxide with an average particle size of 10 to 60 microns so as to give a sunburn prevention effect. When zinc oxide is compounded in a cosmetic, however, secondary agglomeration occurs, and thus a sufficient sunburn preventing action cannot be expected. Further, there is the problem in that the applicability, in particular the feel of use as a cosmetic, deteriorates.

On still another matter, underarm odor, sweat odor, foot odor, hair odor, menstrual odor, and other body odors are frequently explained as deriving from the bacterial decomposition of sweat (for example, see Labows, Kligman, et al, J. Soc. Cosmet. Chem., 34, 1982, page 193). Numerous products are on the market for dealing with such odors. Most of these products include sweat repressants, bactericides, masking agents, and absorbents. Almost all suppressants which reduce the amount of sweat are astringent aluminum compounds. Usually, use is made of aluminum hydroxychloride. On the other hand, as the bactericide for the prevention of a proliferation of bacteria, the cause behind odors, use is often made of hexachlorophene and various quadrary aluminum compounds. Further, as masking agents, use is made of eugenol and other substances having a pleasant odor. These sweat suppressants, bactericides, and masking agents are currently compounded singly or in free combination in products.

However, sweat suppressants act to reduce the source of the sweat odor, the sweat, but complete suppression of sweat is not possible from a biological viewpoint. Considering the action mechanism, further, there is a defect that it is not possible to suppress an already occurring sweat odor.

On the other hand, safety problems have been pointed out for bactericides, which prevent a proliferation of bacteria which break down the sweat and thus lead to the odors. It is not possible to compound them in concentrations enabling a sufficient effect.

Further, masking agents mix with the sweat odors and sometimes, conversely, give rise to an unpleasant smell.

Therefore, conventional deodorants containing sweat suppressors, bactericides, and masking agents suffer from unsatisfactory effectiveness, safety, and practicality in use.

SUMMARY OF THE INVENTION

Accordingly, the objects of the present invention are to eliminate the above-mentioned disadvantages of the prior art and to provide a composite powder in which the surface of core powder is substantially completely covered by a coating powder and deformation of the core powder is minimized.

Another object of the present invention is to provide a process for producing the above-mentioned composite powder.

Still another object of the present invention is to provide a skin treatment agent having a superior adsorption to prior skin waste products.

Still another object of the present invention is to provide a makeup type cosmetic wherein the organic or inorganic spherical powder does not impair the excellent smoothness and easy applicability imparted during practical use of the makeup cosmetic, the spherical core powder is uniformed covered by the coating powder, the coating powder does not separate therefrom no matter what production process the makeup cosmetic passes through, the functionality of the coating powder on the spherical core powder can be imparted in a complete fashion, the hiding power is sufficient, and upon application to the skin, streaking or blotching, uneven color, and color separation can be suppressed, thus giving a beautiful finish.

Still another object of the present invention is to provide a sunburn preventing cosmetic which, in the case of compounding a zinc oxide covering resin powder in the sunburn preventing cosmetic, has a suitable hiding power and gives a natural finish, and exhibits a sufficient ultraviolet scattering ability.

Still another object of the present invention is to provide a deodorant which uses a composite powder comprised of a synthetic resin powder and hydroxyapatite as the active deodorizing ingredient and which is superior in terms of efficacy, safety, and practical use.

Other objects and advantages of the present invention will be apparent from the following description.

In accordance with the present invention, there is provided a composite powder wherein an organic or inorganic core powder is substantially completely covered with one or more types of organic, inorganic, or metallic powders having an average particle size one-fifth or less of the average particle size of the above core powder by means of mixing and compression. The composite powder may be manufactured by mixing and compressing the above core powder and coating powder using a ball mill or other mixer charged with a ball shaped mixing medium having an average diameter of 5 mm or less, thus enabling a composite powder with a uniform particle size and covering and extremely little deformation.

In accordance with the present invention, there is also provided a skin treatment agent wherein an organic or inorganic spherical composite powder having an average particle size of 1 to 100 microns is used as the core powder and hydroxyapatite powder having an average particle size one-fifth or less of the average particle size of the above core powder is used as the coating powder, and they are mixed and compressed so that the spherical core powder is substantially completely covered by the coating powder to form a spherical composite powder which is compounded into the agent. The skin treatment agent is superior to skin treatment agents in which the hydroxyapatite powder is compounded in its original state, in that it has a good feeling during application and is more effective in preventing rough skin, improving rough skin, and suppressing inflammation of the skin for sufferers of acne.

In accordance with the present invention, there is further provided a makeup type cosmetic wherein an organic or inorganic spherical powder having an average particle size of 1 to 100 microns is used as the core powder and one or more types of an organic, inorganic, or metallic powder having an average particle size one-fifth or less of the average particle size of the above core powder is used as the coating powder, and they are mixed and compressed so that the spherical core powder is substantially completely covered by the coating powder to form a spherical composite powder which is compounded into the cosmetic.

In accordance with the present invention, there is still further provided a sunburn preventing cosmetic containing a resin powder covered on the surface thereof with zinc oxide alone or one or more of zinc oxide and another inorganic powder.

In accordance with the present invention, there is still further provided a deodorant which uses a composite powder consisting of a resin powder and one or more of hydroxyapatite, metal oxides, and halogen compounds as a deodorizing active ingredient. The deodorant can be used in the form of, for example, aerosols, roll-ons, powders, lotions, creams, sticks, and other external deodorants, and further, shoe lining and household use type deodorants.

BRIEF DESCRIPTION OF THE DRAWINGS

The present invention will be better understood from the description set forth below with reference to the accompanying drawings, in which.

DESCRIPTION OF THE PREFERRED EMBODIMENTS

Figure 1:
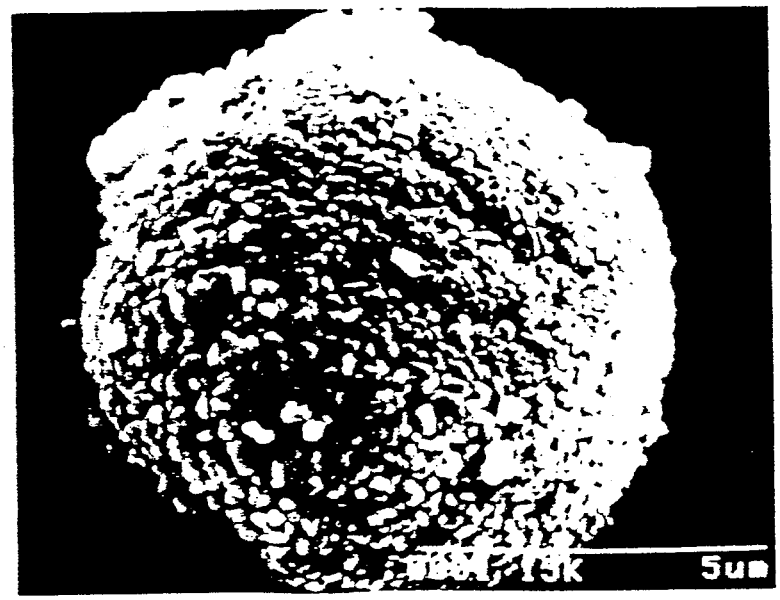
FIG. 1 is an electron micrograph (10000 magnifications) showing the particle structure of the composite powder obtained in Example 1.

In the manufacture of the composite powder according to the present invention, it is most effective to use a substantially spherical powder as the core powder. By making the mixing medium of the apparatus (mixer) used for the mixing and pulverization of conventional solids and the core powder smaller, the effect of mixing and compressing can be optimized. The idea that conventional spherical matter could be mixed and pulverized while maintaining its spherical shape had not been conceived, even by persons skilled in the art. According to the method of the present invention, use is made of spherical powder not considered at all in the prior art, as the core powder, and the surface thereof is substantially completely covered by a coating powder having an average particle size one-fifth or less of the average particle size of the core powder. This is an epochmaking development in view of the standard thinking in the prior art.

As the core powder and the coating powder constituting the composite powder of the present invention, use may be made of any organic or inorganic powder. Representative examples include polyamide resin, polyethylene resin, acrylic resin, polyester resin, fluorine resin, cellulose resin, and other organic powder and titanium dioxide, talc, kaolinite, zinc white, magnesium oxide, calcium oxide, barium sulfate, magnesium carbonate, calcium carbonate, silica, calcium secondary phosphate, iron oxide, chromium oxide, chromium hydroxide, ultramarine blue, prussian blue, hydroxyapatite, and other inorganic powder, or silicon treated, activant treated, wax treated or other treated powder of the same. Any one of these can be used as the core powder. One or more of the above organic or inorganic powder or aluminum powder, gold powder, silver powder, iron powder, or other metallic powders or halogen compounds can be used as the coating powder. There is no particular limitation to the combination of the core powder and coating powder—an organic powder and organic powder, organic powder and inorganic powder, organic powder and metallic powder, inorganic powder and organic powder, inorganic powder and inorganic powder, or inorganic powder and metallic powder—are all acceptable. However, the average particle size of the coating powder with respect to the average particle size of the core powder must be one-fifth or less, preferably one-tenth or less. If the average particle size of the coating powder is greater than one-fifth of that of the core powder, the stability, i.e., non-separation, of the coating powder deteriorates considerably.

The average particle size of the core powder of the composite powder according to the present invention is usually 1 to 100 microns, preferably 3 to 30 microns. As the coating powder, use may be made of resin powder, silica, alumina, magnesium carbonate, talc, kaolinite, mica, and other white colored low index of refraction powders. Even if the index of refraction is low, the hiding power increases in accordance with the reduction of the particle size (until a size of one-half or less of the wavelength of visible light), and thus, with a powder having an average particle size one-fifth or less the size of the core powder, the hiding power of the core powder can be increased, and accordingly, the object of the invention achieved. As the method for manufacturing the composite powder to be compounded in cosmetics in the present invention, an organic or inorganic powder for use as the spherical core powder and one or more types of an organic, inorganic, or metallic powder of an average particle size one-fifth or less the average particle size of the spherical core powder for use as the coating powder are mixed and pulverized, using a continuous or noncontinuous type mixer charged with a ball shaped mixing medium of an average size of 5 mm or less, thereby enabling the core powder to be substantially completely covered by the coating powder. The spherical composite powder obtained by this method of manufacture differs from the conventional powder in that the particle size and the covering are uniform and there is very little deformation.

As the mixer used for the manufacture of the spherical composite powder used in the present invention, mention may be made of a tumbling mill, vibration ball mill, satellite ball mill, sand mill, attriter, or any other mixer. Any of these may be used optimally. However, these mixers conventionally used balls of an average size of 30 mm or less as the mixing medium, and when such a ball mill is used, the core powder and coating powder are sometimes pulverized and deformed and the frequency of contact with the powder is low, so it is sometimes impossible to manufacture a composite powder with the core powder completely covered by the coating powder. Therefore, the ball shaped mixing medium used for the manufacture of the spherical composite powder must be one with an average size of 5 mm or less, preferably, from the viewpoint of good workability, 2 to 5 mm.

As mentioned above, if the ball shaped mixing medium is larger than 5 mm in average size, the core powder cannot be substantially completely covered or deformation or pulverization of the powder will occur, and this is not preferable. There is no particular limitation to the materials of the ball shaped mixing medium of the mixer used in the manufacture of the spherical composite powder: ceramic, metal, or plastic materials may all be used.

There is no particular limitation between the amount of powder and the amount of mixing medium of the mixer in the manufacture of the spherical composite powder, but generally speaking, the larger the amount of mixing medium vis-a-vis the amount of powder, the greater the mixing and compressing effect, and thus the faster the processing is completed, but this in turn readily invites deformation of the spherical composite powder. Further, the lower the amount of mixing medium, the smaller the compressing effect and the longer the processing, but the lower the deformation of the spherical composite powder. Therefore, preferably the amount of mixing medium used is 300 to 700 parts by weight to 100 parts of the overall powder.

In the manufacture of the above-mentioned spherical composite powder, there must be a top open space inside the mixer when the ball-shaped mixing medium is charged therein. A top open space of one-third to two-thirds is preferable.

The temperature of the mixer during processing is not critical so long as it does not impair the properties and shape of the powder used.

Further, the atmosphere in the top open space of the mixture during the processing is not critical. Note that it is preferable to mix the core powder and the coating powder with a Henschel mixer or other general powder mixer before the mixing and compressing treatment. Further, concurrent use may be made of water, alcohol, or other liquids in the powder under treatment by the mixer in the working of the present invention.

As mentioned above, in the manufacture of the composite powder, use is made in the mixer of a ball shaped mixing medium of an average size of 5 mm or less, whereby it is possible to suppress to a minimum the pulverizing effect on the powder and to strikingly increase the frequency of contact, and thus promote a strong bonding of the coating powder adhered to the surface of the core powder by static electricity, etc., which enables the manufacture of a composite powder with a uniform particle size, with the core powder substantially completely covered by the coating powder, and with a superior stability against separation.

Spherical core powder is also used for the spherical composite powder compounded into the makeup type cosmetic of the present invention. In the art of manufacture of such a composite powder, it is most effective to use powder of a substantially spherical shape as the core powder. By making the mixing medium of the apparatus (mixer) used for the mixing and pulverization of conventional solids and the core powder smaller, it is possible to optimize the effect of the mixing and compression. The idea that conventional spherical matter could be mixed and pulverized while maintaining its spherical shape had not been conceived by persons skilled in the art. According to the method of the present invention, use is made of a spherical powder, not considered at all in the prior art, as the core powder, and its surface substantially completely covered by coating powder having an average particle size one-fifth or less of the average particle size of the core powder. This is an epochmaking development in view of the standard thinking in the prior art.

The minimum amount of coating powder required for manufacture of the spherical composite powder according to the present invention is that which will completely cover the core powder in a single particle layer.

"Hydroxyapatite", which is compounded in the skin treatment agent of the present invention, is a mineral name. The mineral is expressed in chemical formula as $Ca_{10}(PO_4)_6(OH)_2$. It is known as an inorganic component of the bones of vertebrates. Almost all of the naturally produced apatite minerals are fluoro apatite, i.e., $Ca_{10}(PO_4)_6F_2$, since the hydroxyapatite powder is usually synthesized by the wet or dry method as mentioned below. As an example of the wet method, calcium hydroxide and phosphoric acid are reacted in an aqueous solution at a temperature from room temperature to about 60° C. to obtain hydroxyapatite powder. On the other hand, as an example of the dry method, calcium carbonate and calcium phosphate are solid phase reacted in air or in a steam atmosphere at a high temperature of 900° C. to 1200° C. to obtain the hydroxyapatite. When a fine particle form of hydroxyapatite powder is required, the wet method is preferable.

The average particle size of the hydroxyapatite must be one-fifth or less, preferably one-tenth or less, of the average particle size of the core powder. If the average particle size of the hydroxyapatite is larger than one-fifth that of the core powder, the stability of the hydroxyapatite against separation will decline considerably, which is not preferable.

The skin treatment agent of the present invention may contain, in addition to the above-mentioned composite powder, cosmetics, pharmaceuticals, quasi-drugs, and other components in general use.

For example, it may also contain talc, kaolinite, mica, sericite, muscovite, phlogophite, synthetic mica, lepidolite, biotite, lithia mica, vermiculite, magnesium carbonate, calcium carbonate, diatomaceous earth, magnesium silicate, calcium silicate, aluminum silicate, barium silicate, barium sulfate, strontium silicate, metal salts of tungstate, silica, zeolite, boron nitride, ceramic powder, and other inorganic powder, nylon powder, polyethylene powder, benzoguanamine powder, tetrafluoroethylene powder, fine crystalline cellulose, and other organic powder, titanium oxide, zinc oxide, and other inorganic white pigments, iron oxide (red iron oxide), iron titanate, and other inorganic red pigments, gamma-iron oxide, and other inorganic brown pigments, yellow iron oxide, yellow ochre, and other inorganic yellow pigments, black iron oxide, carbon black, and other inorganic black pigments, manganese violet, cobalt violet, and other inorganic purple pigments, chromium oxide, chromium hydroxide, cobalt titanate, and other inorganic green pigments, ultramarine blue, prussian blue, and other inorganic blue pigments, titanium oxide coated mica, titanium oxide coated bismuth oxychloride, bismuth oxychloride, titanium oxide coated talc, guanine, colored titanium oxide coated mica, and other nacreous pigments, aluminum powder, copper powder, and other metal powder dyes, C.I. 15850, C.I. 15585, C.I. 15630, C.I. 15880, C.I. 73360, C.I. 12085, C.I. 15865, C.I. 12075, C.I. 21110, C.I. 15510, C.I. 11680, C.I. 74160, C.I. 45430, C.I. 45410, C.I. 45100, C.I. 17200, C.I. 45380, C.I. 45190, C.I. 12140, C.I. 15510, C.I. 19140, C.I. 15985, C.I. 45350, C.I. 47005, C.I. 42053, C.I. 42090, zirconium, barium or aluminum lake organic pigments, chlorophyll, betacarotene, and other natural colors, squalane, liquid paraffin, vaseline, microcrystalline wax, ozocerite, ceresine, cetyl alcohol, hexadecyl alcohol, oleyl alcohol, cetyl-2-ethylhexanoate, 2-ethylhexylpalmitate, 2-octyldecylmyristate, 2-octyldodecyl gum ester, neopentyl glycol-2-ethylhexanate, glyceryl triisooctate, 2-octyldodecyl oleate, isopropylmyristate, glyceryl triisostearate, coconut oil fatty acid triglyceride, olive oil, avocado oil, lanolin, dimethylpolysiloxane, and other hydrocarbons, oils and fats, esters, higher alcohols, waxes, silicone oil, and other oils, ultraviolet absorbents, antioxidants, preservatives, surfactants, moisture retainers, perfumes, water, alcohol, and thickening agents.

The zinc oxide used in the sunburn preventing cosmetics of the present invention may be any in general use for cosmetics, but in general has an average particle size of 0.01 to 1 micron, preferably 0.01 to 0.1 micron.

The resin powder referred to in the present invention preferably includes polyester, polyethylene, polystyrene, polymethyl methacrylate, cellulose, chitin, chitosan, 12 nylon, 6 nylon, epoxy resin, acrylic resin, metacrylic resin, teflon, polyvinyl chloride. The resin powder may be spherical or amorphous in shape and may be porous or nonporous. The powder used is one with an average particle size of 1 to 100 microns or so, and is selected so that the average particle size of the zinc oxide is in a range of 1/1000 to 1/5 the average particle size of the resin powder.

In the manufacture of the zinc oxide covered resin powder of the present invention, zinc oxide and resin powder are mixed by the wet or dry method, for example. As the mixer, various ball mills, pot mills, automated mortars, automatic mortars, attriters, etc. may be appropriately used.

The ratio of amounts used when mixing the zinc oxide and resin powder should be 0.1 to 200 parts of zinc oxide to 100 parts of resin powder.

At this time, as the powder adhered to the resin powder, use may be made, in addition to the zinc oxide, of other inorganic powder, for example, talc, mica, titanium oxide, kaolinite, chrome oxide, yellow iron oxide, red iron oxide, black iron oxide, barium sulfate, prussian blue, ultramarine blue, aluminum hydroxide, aluminum silicate, silicic acid anhydride, silicic acid hydrate, and the like to an extent wherein the effects of the present invention are not impaired.

The zinc oxide covered resin powder may be compounded in the sunburn preventing cosmetic as it is, or may be subjected first to surface reformation as commonly used for cosmetic powder for improving the dispersion stability and usability, e.g., may be treated with an activant, metallic soap, or silicone.

The amount of the zinc oxide covered resin powder compounded in the sunburn preventing cosmetic should be 0.1 to 60 percent, preferably 0.5 to 20 percent. When less than 0.1 percent, a sufficient ultraviolet scattering effect cannot be expected. When over 60 percent, it is not practical in terms of the feeling during use.

The sunburn preventing cosmetic of the present invention may include, in addition to the above-mentioned essential component, oils, water, surfactants, moisture retainers, thickening agents, perfumes, medicines, antioxidants, chelating agents, colors, preservatives and antibacterial agents, ultraviolet absorbents, and other components usually used in cosmetics in accordance with the application of the product to a quantity and quality that do not impair the effects of the present invention.

The sunburn preventing cosmetic of the present invention may be a powder, cream, paste, stick, lotion, or the like in form and is not restricted to any of the same.

As the resin powder used as a component of the deodorant of the present invention, mention may be made of nylon, polyvinyl alcohol, polyvinyl chloride, polyester, polyethylene, polypropylene, polyvinylidene cyanide, polyurea, polystyrene, polyurethane, polyfluoroethylene, epoxy resin, acrylic resin, methacrylic resin, cellulose, chitin, chitosan, etc. Preferably, nylon, polyethylene, and polypropylene, especially preferably nylon, are used.

The deodorant according to the present invention uses as its active deodorizing ingredient a composite powder constituted of the above-mentioned resin powder and hydroxyapatite; metal oxides such as zinc oxide, magnesium oxide, and calcium oxide; and/or halogen compounds hexachlorophene, benzethonium chloride, aluminum hydroxychloride, aluminum zirconium chlorohydrate, berberine chloride, chlorophyllin-copper complex, sodium copper chlorophyllin, and benzalkonium chloride. Preferably hydroxyapatite, zinc oxide, and aluminum hydroxychloride. These deodorant components may be preferably compounded in the deodorant in an amount 0.1 to 60 percent by weight. As other components of the deodorant, any known component can be used.

As such components, mention may be made of avocado oil, almond oil, olive oil, grapeseed oil, sesame oil, sasanqua oil, safflower oil, soybean oil, camelia oil, corn oil, rapeseed oil, persic oil, castor oil, sunflower oil, cottonseed oil, peanut oil, cocoa oil, palm oil, coconut oil, milkfat, fish oil, hardened oil, turtle oil, hog oil, mink oil, egg yolk oil, and other oils and fats, spermaceti, shellac, bees wax, lanolin, liquid lanolin, carnauba wax, candelilla wax, and other waxes, liquid paraffin, liquid polyisobutylene, squalane, pristane, vaseline, paraffin, ceresine, and other hydrocarbons, ethanol, isopropanol, lauryl alcohol, cetanol, 2-hexyl decanol, stearyl alcohol, isostearyl alcohol, oleyl alcohol, lanolin alcohol, and other alcohols, ethylene glycol, diethylene glycol monoethylether, triethylene glycol, polyethylene glycol, propylene glycol, 1,3-butylene glycol, glycerine, batyl alcohol, and other polyhydric alcohols, glucose, cane sugar, milk sugar, xylitol, sorbitol, mannitol, maltiol, and other sugars, diisopropyl adipate, hexyldecyl isostearate, cetyl isooctate, oleyl oleate, decyl oleate, lanolin acetate, butyl stearate, isopropyl myristate, diethyl phthalate, hexyl laurate, and other esters, aluminum stearate, magnesium stearate, zinc stearate, and other metal soaps, arabic gum, sodium alginate, caseine, carrageenan, karaya gum, agar-agar, quince seed, gelatin, dextrin, starch, tragacanth, pectin, and other natural water soluble polymer compounds, propylene glycol alginate, ethyl cellulose, crystalline cellulose, methyl cellulose, and other semisynthetic polymer compounds, carboxyl vinyl polymers, polyvinyl methyl ethers, metoxyethylene maleic anhydride copolymers, and other synthetic polymer compounds, dialkylsulfosuccinic acid salts, alkylarylsulfonic acid salts, higher alcohol ester sulfate salts, ester phosphate salts, and other surfactants, ethyl parahydroxybenzoate, methyl parahydroxybenzoate, and other preservatives, vitamin A, vitamin D, vitamin E, vitamin K, and other vitamins, estradiol, ethynylestradiol, cortisone, and other hormones, C.I. 16185, C.I. 42090, C.I. 15850, C.I. 45350, C.I. 59040, C.I. 60725, and other organic colors, aluminum powder, talc, kaolinite, bentonite, mica, titanium-coated mica, red iron oxide, carmine, and other inorganic colors, urocanic acid, cynoxate, and other ultraviolet absorbents, allantoin, aloe powder, guaiazulene, and other inflammation suppressants, Freon 113, Freon 114, Freon C 318, methylchloride, methylene chloride, isobutane, carbonic acid gas, and other propellants, and purified water.

As other additives which can be compounded at will with the deodorant according to the present invention, mention may be made of aluminum hydroxychloride, aluminum chloride, aluminum sulfate, basic aluminum bromide, aluminum phenolsulfonic acid, tannic acid, aluminum naphthalene sulfonic acid, basic aluminum iodide, and other sweat suppressants, 3,4,4-trichlorocarbanilide (TCC), benzalkonium chloride, benzethonium chloride, alkyltrimethylammonium chloride, resorcinol, phenol, sorbic acid, salicylic acid, hexachlorophene, and other bactericides, musk, skatole, lemon oil, lavender oil, absolute, jasmine, vanillin, benzoin, benzyl acetate, menthol, and other masking agents.

The composite powder comprised of the resin powder and hydroxyapatite, compounded as an essential component of the deodorant of the present invention, can be manufactured by any method, but preferably a resin powder is used as the core powder and the core powder is substantially completely covered with hydroxyapatite having an average particle size one-fifth or less of the resin powder.

The ratio of the amount of the resin powder and the coating powder used may be changed arbitrarily depending on the form of the product and is not particularly limited, but preferably the percent by weight of the hydroxyapatite to the resin powder is from 5 to 60 percent. Further., the particle size of the synthetic resin powder is not particularly limited, but is preferably about 0.5 to 20 microns when used for a deodorant applied to the skin, etc.

The composite powder compounded as the active deodorizing ingredient in the deodorant of the present invention can be manufactured by the mixing technique. That is, it is possible to use a tumbling mill, vibration ball mill, satellite ball mill, sand mill, attriter, or any other mixer. Further, if the ball shaped mixing medium of the ball mills etc. used has an average particle size of 5 mm or less, a composite powder can be obtained wherein, for example, the surface of the resin powder is substantially completely covered with hydroxyapatite powder by strong compression, and thus the stability against separation is high (i.e., the hydroxyapatite will not easily separate from the surface of the synthetic resin powder).

According to the present invention, as mentioned above, the surface of the core powder is substantially completely covered by a powder serving as a coating powder, enabling an improvement of the surface characteristics of the core powder. For example, by covering the surface of a spherical core powder with a coating powder having hiding power, a spherical composite powder having an excellent smoothness and hiding power can be made, the surface of a hydrophilic core powder can be covered with a water repellant coating powder to give water repellency, or conversely, the surface of a water repellent core powder can be covered with a hydrophilic coating powder to give hydrophilicity, the surface of a low specific gravity core powder can be covered with a high specific gravity coating powder to make a low specific gravity powder, the surface of a spherical core powder can be covered with a colored coating powder with a poor smoothness to make a colored composite powder with a good smoothness, and the surface of a nonmagnetic core powder can be covered with a magnetic coating powder to make a magnetic composite powder, etc. Thus a tremendous effect is obtained in that the surface characteristics of all sorts of powders can be improved.

The skin treatment agent of the present invention has a superior feel during application and adsorbs the decomposed sebum, i.e., products of decomposition of triglyceride, that is, free fatty acids, and various liquid peroxides arising due to oxidation deterioration, thus maintaining the skin in its normal state and further preventing rough skin, improving skin roughness, and suppressing the skin inflammation of acne sufferers.

The sunburn preventing cosmetic of the present invention has a superior effectiveness in protecting the skin from hazardous ultraviolet rays. This is believed to be because the zinc oxide covered resin powder adheres uniformly to the surface of the resin powder in a simple dispersed state with the secondary agglomeration of the zinc oxide completely eliminated. Further, at the same time, it has an excellent practical use and cosmetic finish. The inherent characteristics of zinc oxide, i.e., the astringency and inflammation suppression effects, can be simultaneously enjoyed. The deodorant of the present invention has an efficient deodorizing effects with superior safety and practical applicability.

EXAMPLES

The present invention will now be further illustrated by, but is by no means limited to, the following examples, wherein all parts and percentages are expressed on a weight basis unless otherwise noted.

EXAMPLE 1

A 65.0 part amount of spherical Nylon 12 powder (average particle size 6.6 microns) and 35.0 parts of titanium dioxide powder (average particle size 0.2 micron) were mixed together in a Henschel mixer (Mitsui Miike Machinery Co., Ltd., Model FM10B) for 5 minutes, then the obtained mixed powder was mixed and compressed in a tumbling mill (Yamato Scientific Co., universal ball mill) charged with alumina balls (Nippon Kagaku Togyo Co., HD alumina balls, 3 mm$\phi$) for 14 hours. Inspection by a scanning type electron microscope (Hitachi Ltd., Model S-510 scanning electron microscope) confirmed that a composite powder with a particle structure shown in FIG. 1 was obtained. This composite powder was spherical in shape, featured Nylon 12 spherical powder substantially completely covered by titanium dioxide powder, displayed a suitable hiding power and hydrophilicity, and had an excellent smoothness. Further, it had a superior stability against separation of the coating powder due to shearing force, etc.

The evaluation of the smoothness was made by measurement of the coefficient of dynamic friction. Note that the powder friction test apparatus (Journal of the Society of Powder Technology, vol. 21, No. 9, p. 565, 1984) was a special order item, and featured an iron plate set horizontally, to which a double sided tape was attached. The sample was set thereon, and a load (5 to 70 g/cm$^2$) was applied to an aluminum attachment. The slipping stress when the attachment was moved right and left at a speed of 10 mm per second was measured by a strain gauge and the coefficient of kinetic friction obtained from the relationship of the load and slipping stress.

Figure 2:
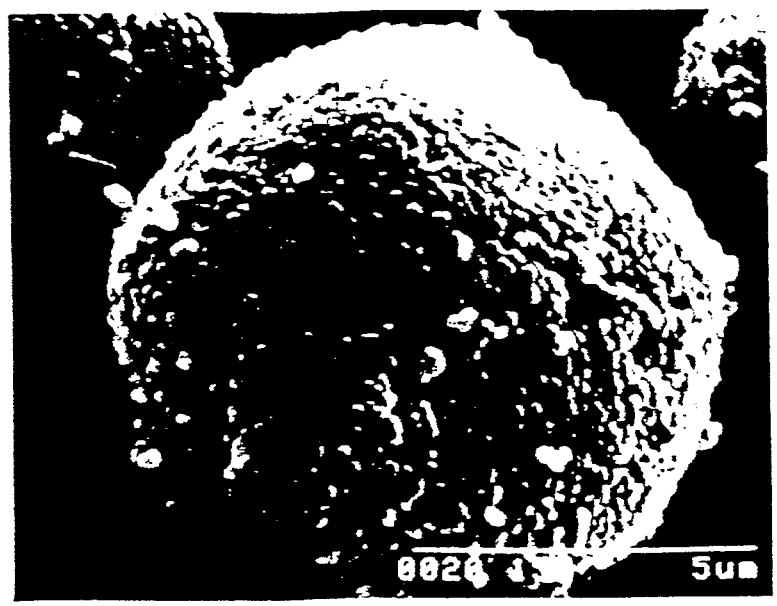
FIG. 2 is an electron micrograph (10000 magnifications) showing the particle structure of the composite powder obtained in Example 1 after colloid milling.

The coefficient of dynamic friction of the composite powder obtained was 0.38, a considerably low value compared with the 0.60 of titanium dioxide and about the same level as the 0.39 of Nylon 12 spherical powder, and thus indicated a good smoothness. The hiding power was measured by a cryptometer. The hiding power of the composite powder was high—corresponding to 30 percent of the titanium dioxide powder. Further as a test of the stability against separation of the coating powder, the obtained composite powder was dispersed in liquid paraffin to make a slurry and then subjected to colloid milling. The coating powder did not separate due to the milling, as shown by observation of the particle structure of the tested powder by a scanning type electron microscope (Hitachi Ltd., Model S-510 electron microscope) (FIG. 2).

COMPARATIVE EXAMPLE 1

In the same way as in Example 1, 63.0 parts of Nylon 12 spherical powder (average particle size 6.6 microns) were mixed with 37.0 parts of titanium dioxide powder (average particle size 0.2 micron) in a Henschel mixer (Mitsui Miike Machinery Co., Ltd., FM10B) for 5 minutes. Next, the mixed powder was placed in a tumbling mill (Yamato Scientific Co., universal ball mill) charged with alumina balls (Nihon Kagaku Tokyo Co., HD alumina balls 20 mm$\phi$) and mixed and compressed for 14 hours.

Figure 3:
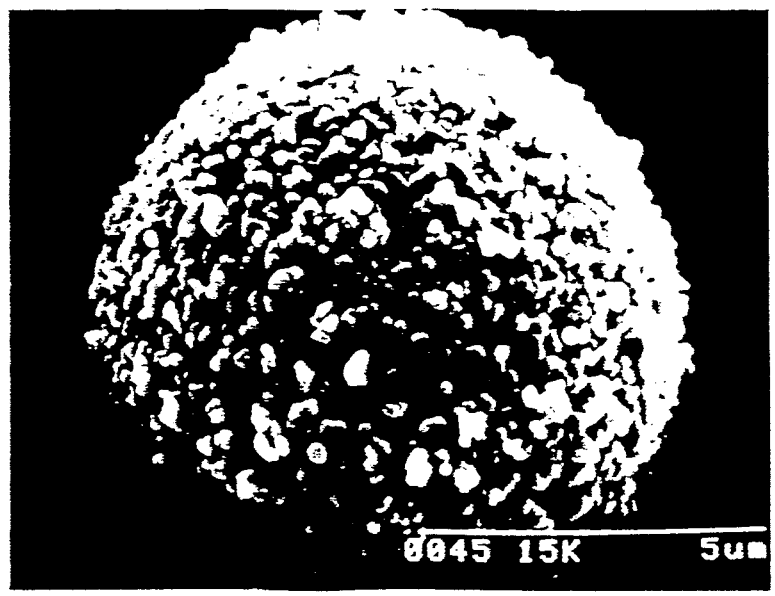
FIG. 3 is an electron micrograph (10000 magnifications) showing the particle structure of the composite powder obtained in Comparative Example 1.
Figure 4:
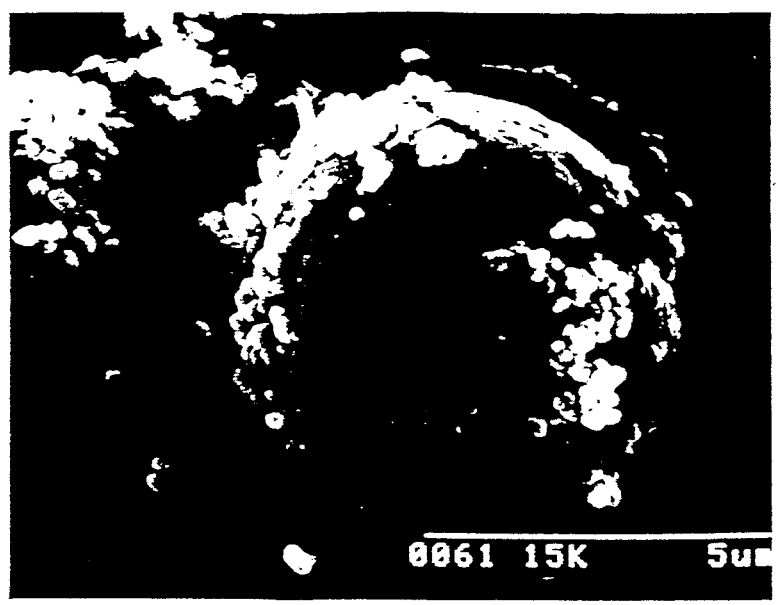
FIG. 4 is an electron micrograph (10000 magnifications) showing the particle structure of the composite powder obtained in Comparative Example 1 after colloid milling.

The obtained powder, as clear from the results of observation by the scanning type electron microscope (Hitachi Ltd., Model S-510 scanning electron microscope), which are shown in FIG. 3, featured Nylon 12 spherical powder which was not completely covered by the titanium dioxide powder and conspicuous gaps appeared on the surface of the composite powder. Note that even if the composite powder were further mixed for a long time, the covering would remain uncomplete and, further, the Nylon 12 spherical powder would be deformed and destroyed. The composite powder shown in FIG. 3 had hiding power and displayed hydrophilicity, but the coefficient of dynamic friction was 0.45 and thus the smoothness was extremely poor. A test was run on the stability against separation of the coating powder in the same way as in Example 1 with colloid milling. Observation of the particle structure by a scanning type electron microscope (Hitachi Ltd., Model S-510 scanning electron microscope) confirmed, as shown in FIG. 4, conspicuous separation of the coating powder.

EXAMPLE 2

A 60.0 part portion of hydrophilic calcium secondary phosphate powder (average particle size 30 microns) was mixed with 40.0 parts of hydrophobic polystyrene powder (average particle size 3 microns) in a Henschel mixer (Mitsui Miike Machinery Co., Ltd., FM10B) for 5 minutes, then the obtained mixed powder was placed in a vibration ball mill (Nihon Spindle Seizo Co., TKM) charged with alumina balls (Nippon Kagaku Togyo Co., HD alumina balls, 5 mm$\phi$) and mixed and compressed for 2 hours.

The obtained composite powder featured calcium secondary phosphate powder substantially completely covered by the polystyrene powder, displayed hydrophobicity, and had an improved smoothness compared with the core powder, calcium secondary phosphate.

EXAMPLE 3

A 65.0 part portion of hydrophobic polystyrene powder (average particle size 15 microns) was mixed with 35.0 parts of hydrophilic spherical silica powder (average particle size 2 microns) in a small sized pulverizer (Kyoritsu Riko Co., SK-M10) for 1 minute, then the obtained mixed powder was placed in a satellite mill (Mitamura Riken Kogyo Co., centrifugal ball mill) charged with alumina balls (Nippon Kagaku Tokyo co., HD alumina balls, 2 mm$\phi$) and mixed and compressed for 1 hour.

The obtained composite powder featured substantially complete coverage and displayed hydrophilicity.

EXAMPLE 4

A 70.0 part amount of cellulose spherical powder (average particle size 3 microns) was mixed and compressed with 30.0 parts of ultramarine blue (average particle size 0.3 micron) in a tumbling mill (Yamato Scientific Co., universal ball mill) charged with alumina balls (Nippon Kagaku Togyo Co., HD alumina balls, 3 mm$\phi$) for 10 hours.

The obtained composite powder featured substantially complete coverage and had a significantly improved smoothness compared with ultramarine blue.

EXAMPLE 5

A 72.0 part amount of nonmagnetic polystyrene spherical powder (average particle size 8 microns) was placed with 28.0 parts of magnetic iron oxide (average particle size 0.3 micron) in a vibration ball mill (Nihon Spindle Seizo Co., VKM-2) charged with alumina balls (Ashizawa alumina balls, 2 mm$\phi$) and mixed and compressed for 3 hours.

The obtained composite powder featured substantially complete coverage and displayed magnetic properties and hydrophilicity.

EXAMPLE 6

15 A 61.0 part portion of spherical polystyrene powder (average particle size 100 microns) was placed with 9.0 parts of aluminum powder (average particle size 5 microns) in a satellite mill (Mitamura Riken Kogyo Co., centrifugal ball mill) charged with alumina balls (Ashizawa alumina balls, 1 mm$\phi$) and mixed and compressed for 30 minutes.

The obtained composite powder featured substantially complete coverage and the outer appearance thereof had a metallic luster.

EXAMPLE 7: FACIAL FOUNDATION

| Component | (Composition) (%) |
|---|---|
| (1) 40% titanium oxide covered spherical cellulose* | 15.0 |
| (2) Silicone treated mica | 40.0 |
| (3) Silicone treated talc | 20.45 |
| (4) Silicone treated iron oxide | 6.5 |
| (5) Titanium oxide | 5.0 |
| (6) Trimethylolpropane triisostearate | 5.0 |
| (7) Squalane | 3.0 |
| (8) Beeswax | 2.0 |
| (9) Sorbitan trioleate | 1.0 |
| (10) Preservative | 0.5 |

-continued

| Component | (Composition) (%) |
|---|---|
| (11) Vitamin E | 0.05 |
| (12) Butylmethoxybenzoylmethane | 1.0 |
| (13) Perfume | 0.5 |

*In the same way as in Example 1, 60 parts of spherical cellulose powder (average particle size 20 microns) were mixed with 40 parts of titanium dioxide powder (average particle size 0.2 micron) in a Henschel mixer for 5 minutes, then the obtained mixed powder was mixed and compressed in a vibration ball mill charged with alumina balls (Nippon Kagaku Tokyo Co., HD alumina balls, 2 mm$\phi$) for 20 hours.

Production Process

Components (1) to (5) were mixed in a Henschel mixer. To this was added and mixed a mixture of components (6) to (13) heated and melted together. This was then pulverized and shaped into a shallow dish form to give a facial foundation. The foundation had covering power, and at the same time, was easy to apply and gave a beautiful finish.

EXAMPLE 8: OILY FOUNDATION

| Component | (Composition) (%) |
|---|---|
| (1) Titanium oxide | 6.0 |
| (2) 35% titanium oxide covered spherical nylon powder* | 7.0 |
| (3) Kaolinite | 12.0 |
| (4) Muscovite | 23.7 |
| (5) Red iron oxide | 1.0 |
| (6) Yellow iron oxide | 0.7 |
| (7) Black iron oxide | 0.1 |
| (8) Squalane | 27.0 |
| (9) Cetyl 2-ethylhexanate* | 16.0 |
| (10) Sorbitan sesquioleate | 1.0 |
| (11) Aristo wax | 4.0 |
| (12) Carnauba wax | 1.3 |
| (13) Perfume | 1.3 |

*In the same way as in Example 1, 65.0 parts of spherical Nylon 12 powder (average particle size 6.6 microns) were mixed with 35 parts of titanium dioxide powder (average particle size 0.2 micron) in a Henschel mixer for 5 minutes, then the obtained mixed powder was mixed and compressed in a tumbling mill charged with alumina balls (Nippon Kagaku Tokyo Co., HD alumina balls, 3 mm$\phi$) for 14 hours.

Production Process

Components (8) and (9) and component (10) were mixed at 80° C. To this were added components (1), (2), (3), (4), (5) to (6), and (7). These were mixed with a mixer, then subjected to colloid milling. On the other hand, components (11) and (12) were heated to melting point, then added to and mixed with the above-mentioned mixture. The entire mixture was deaerated, then component (13) slowly mixed in. This was then filled into a shallow dish at 80° C. and cooled, thereby giving the oily foundation.

COMPARATIVE EXAMPLES 2 AND 3

In the composition of Example 8, component (2) was replaced by the composite powder of Example 2 (Comparative Example 2) or untreated nylon powder (Comparative Example 3). This was then prepared by the same method as in Example 8.

An organoleptic evaluation was conducted on the products of Example 8 and Comparative Examples 2 and 3, the results being shown in Table 1. As to the method of evaluation, a panel of 10 experts rated the products in five stages, 1 to 5. The following symbols indicate the average values:

◎ ... 4.5 to 5.0
○ ... 3.5 to 4.4

TABLE 1

| Sample | Application | Covering power | Closeness of feel | Streaking/blotch | Finish | General |
|---|---|---|---|---|---|---|
| Ex. 8 | ○ | ◎ | ○ | ◎ | ◎ | ◎ |
| C. Ex. 2 | △ | ○ | x | x | x | △ |
| C. Ex. 3 | ○ | △ | x | xx | xx | x |

As clear from Table 1, the oily foundation of the present invention is superior to those of the conventional comparative examples in all items of the organoleptic evaluation. The same conclusion as in the example can be drawn for oily stick foundations wherein the product is filled into a stick-like container.

EXAMPLE 9: POWDER FOUNDATION

| Component | (Composition) (%) |
|---|---|
| (1) 30% titanium oxide covered polyethylene* | 16.0 |
| (2) Talc | 20.8 |
| (3) Muscovite | 50.0 |
| (4) Red iron oxide | 0.7 |
| (5) Yellow iron oxide | 1.0 |
| (6) Black iron oxide | 0.1 |
| (7) Silicone oil | 1.0 |
| (8) Cetyl 2-ethylhexanoate | 9.0 |
| (9) Sorbitan sesquioleate | 1.0 |
| (10) Preservative | 0.3 |
| (11) Perfume | 0.1 |

*In the same way as in Example 1, 70.0 parts of spherical polyethylene (average particle size 4 microns) were mixed with 30 parts of titanium dioxide (average particle size 0.3 micron) in a Henschel mixer for 5 minutes, then the obtained mixed powder was mixed and compressed in a tumbling mill charged with alumina balls (Nippon Kagaku Tokyo Co., HD alumina balls 5 mmφ) for 8 hours.

Production Process

Components (1) to (6) were mixed in a Henschel mixer. To this was added and mixed a mixture of components (9) to (11) heated and melted together. This was then pulverized and shaped into a shallow dish form to give a powder foundation. The powder foundation was easy to apply and gave a beautiful finish.

EXAMPLE 10: BRUSHER

| Component | (Composition) (%) |
|---|---|
| (1) Talc | 15.0 |
| (2) Sericite | 65.0 |
| (3) 10% red iron oxide covered spherical cellulose* | 4.0 |
| (4) 5% yellow iron oxide covered spherical cellulose** | 2.0 |
| (5) 5% ultramarine blue covered spherical cellulose*** | 2.0 |
| (6) C.I. 15630 | 0.1 |
| (7) Titanium mica type pearling agent | 3.0 |
| (8) Squalane | 3.0 |
| (9) 2-Ethylhexyl palmitate | 5.0 |
| (10) Preservative | 0.3 |
| (11) Perfume | 0.1 |

*In the same way as in Example 1, 90 parts of spherical cellulose (average particle size 20 microns) were mixed with 10 parts of red iron oxide (average particle size 0.1 micron) in a Henschel mixer for 5 minutes, then the obtained mixed powder was mixed and compressed in a tumbling mill charged with alumina balls (Nippon Kagaku Togyo Co., HD alumina balls, 3 mmφ) for 12 hours.
**In the same way as in Example 1, 95 parts of spherical cellulose (average particle size 20 microns) were mixed with 5 parts of yellow iron oxide (average particle size 0.2 micron) in a Henschel mixer for 5 minutes, then the obtained mixed powder was mixed and compressed in a tumbling mill charged with alumina balls (Nippon Kagaku Togyo Co., HD alumina balls, 3 mmφ) for 12 hours.
***In the same way as in Example 1, 95 parts of spherical cellulose (average particle size 20 microns) were mixed with 5 parts of ultramarine blue (average particle size 2 microns) in a Henschel mixer for 5 minutes, then the obtained mixed powder was mixed and compressed in a tumbling mill charged with alumina balls (Nippon Kagaku Togyo Co., HD alumina balls, 3 mmφ) for 12 hours.

Production Process

Components (1) to (6) were mixed in a Henschel mixer. To this was sprayed and mixed a mixture of components (8) to (11) heated and melted together. This was then pulverized, added with component (7) and mixed, then shaped into a shallow dish form to give the brusher.

COMPARATIVE EXAMPLE 4

In the Composition of Example 10, components (3), (4), and (5) were replaced with 0.4 percent red iron oxide, 0.1 percent yellow iron oxide, 0.1 percent ultramarine blue, and 7.4 percent spherical cellulose. Otherwise, the same procedure was followed as in Example 10 to make the brusher.

The brusher of Example 10 featured no uneven color, unlike that of Comparative Example 4.

EXAMPLE 11: Lipstick

| Component | (Composition) (%) |
|---|---|
| (1) Hydrocarbon wax | 3.0 |
| (2) Candelilla wax | 1.0 |
| (3) Glyceryl isostearate | 40.0 |
| (4) Liquid paraffin | 44.0 |
| (5) Titanium oxide | 2.0 |
| (6) 10% C.I. 15585 covered spherical methyl methacrylate resin* | 6.8 |
| (7) Organic pigment | 3.0 |
| (8) Perfume | 0.2 |

*In the same way as in Example 1, 90 parts of spherical methyl metacrylate resin (average particle size 10 microns) were mixed with 10 parts of Red No. 204 (average particle size 0.2 micron) in a Henschel mixer for 5 minutes, then the obtained mixed powder was mixed and compressed in a tumbling mill charged with alumina balls (Nippon Kagaku Togyo Co., HD alumina balls, 3 mmφ) for 14 hours.

Production Process

Components (1) to (4) were heated and melted at 85° C. To this was added and stirred components (5) to (7). Next, component (8) was mixed in with stirring. This was filled into a container to make the lipstick. The lipstick featured no color separation and was easy to apply.

EXAMPLE 12: Emulsified Foundation

| Component | (Composition) (%) |
|---|---|
| (1) Stearic acid | 0.4 |
| (2) Isostearic acid | 0.3 |

-continued

(Composition)

| Component | (%) |
|---|---|
| (3) Cetyl 2-ethylhexanoate | 4.0 |
| (4) Liquid paraffin | 11.0 |
| (5) POE (10) stearyl ester | 2.0 |
| (6) Talc | 15.0 |
| (7) 50% pigment covered spherical polyethylene* | 7.0 |
| (8) Cetyl alcohol | 0.3 |
| (9) Preservative | 0.09 |
| (10) Triethanol amine | 0.42 |
| (11) Propylene glycol | 5.0 |
| (12) Ion exchange water | 54.19 |
| (13) Perfume | 0.3 |

*In the same way as in Example 1, 50 parts of spherical polyethylene powder (average particle size 5 microns) were mixed with 40 parts of titanium dioxide (average particle size 0.2 micron), 3.5 parts of red iron oxide (average particle size 0.1 micron), 5.5 parts of yellow iron oxide (average particle size 0.2 micron), and 1 part of black iron oxide (average particle size 0.2 micron) in a Henschel mixer for 5 minutes, then the obtained mixed powder was mixed and compressed in a tumbling mill charged with alumina balls (Nippon Kagaku Togyo Co., HD alumina balls, 3 mmϕ) for 12 hours.

Production Process

Components (1) to (9) were heated, melted and mixed at 85° C. To this was gradually added a mixture of components (10) to (12) which were heated, melted, and mixed at 85° C., for emulsification. The temperature at the time of emulsification was held for 10 minutes and the mixture stirred. It was then cooled, while stirring, to 45° C. To this was added component (13). The cooling and stirring continued until 35° C., then the product was taken out and filled into a container to make the emulsified foundation. The emulsified foundation featured no uneven color or color separation and was easy to apply.

EXAMPLE 13: Eyeliner

(Composition)

| Component | (%) |
|---|---|
| (1) Black iron oxide | 3.0 |
| (2) 50% ultramarine blue covered spherical alumina* | 4.0 |
| (3) Vinyl acetate resin emulsion | 45.0 |
| (4) Glycerin | 5.0 |
| (5) Polyoxyethylene (20 mol) sorbitan monooleate | 1.0 |
| (6) Carboxymethylcellulose (10% aqueous solution) | 15.0 |
| (7) Acetyltributyl citrate | 1.0 |
| (8) Purified water | 19.0 |
| (9) Perfume | Suitable amt |
| (10) Preservative | Suitable amt |

*In the same way as in Example 1, 50 parts of spherical alumina (average particle size 25 microns) were mixed with 50 parts of ultramarine blue (average particle size 2 microns) in a Henschel mixer for 5 minutes, then the obtained mixed powder was mixed and compressed in a vibration ball mill charged with alumina balls (Nippon Kagaku Togyo Co., HD alumina balls, 4 mmϕ) for 24 hours.

Production Process

To component (8) were added components (4) and (5). These were heated to dissolve, then added with components (1) and (2) and subjected to colloid milling (dye portion). The other components were mixed and heated at 70° C. To this was added the above dye portion. This was uniformly dispersed by a homogenizer. As a result, an eyeliner with no color separation and with which lines could be smoothly drawn, was obtained.

EXAMPLE 14: Eyeshadow

(Composition)

| Component | (%) |
|---|---|
| (1) 25% black iron oxide and 25% prussian blue covered spherical silica* | 10.0 |
| (2) 25% red iron oxide and 25% yellow iron oxide covered spherical silica** | 3.0 |
| (3) Talc | 7.0 |
| (4) Kaolinite | 15.0 |
| (5) Nacreous pigment | 15.0 |
| (6) Japan wax | 20.0 |
| (7) Stearic acid | 10.0 |
| (8) Beeswax | 5.0 |
| (9) Hardened castor oil | 5.0 |
| (10) Vaseline | 4.0 |
| (11) Lanolin | 3.0 |
| (12) Squalane | 3.0 |
| (13) Preservative, antioxidant | Suitable amt |

*A 50 part amount of spherical silica (average particle size 10 microns) was mixed with 25 parts of black iron oxide (average particle size 0.2 micron) and 25 parts of prussian blue (average particle size 0.1 micron) in a Henschel mixer for 5 minutes, then the obtained mixed powder was mixed and compressed in a tumbling mill charged with alumina balls (Nippon Kagaku Tokyo Co., HD alumina balls, 3 mmϕ) for 24 hours.

**In the same way as in Example 1, 50 parts of spherical silica (average particle size 10 microns) were mixed with 25 parts of red iron oxide (average particle size 0.1 micron) and 25 parts of yellow iron oxide (average particle size 0.2 micron) in a Henschel mixer for 5 minutes, then the obtained mixed powder was mixed and compressed in a tumbling mill charged with alumina balls (Nippon Kagaku Togyo Co., HD alumina balls, 3 mmϕ) for 24 hours.

Production Process

Components (1) to (5) were mixed well with a blender (powder portion). The other components were mixed, heated and melted, then the above powder portion added thereto and the mixture kneaded well and shaped into a core. This was placed between wood to make a pencil form. An eyeshadow was obtained which had no uneven color and an easy applicability.

EXAMPLE 15: Solid Powder Form Skin Treatment Agent

(Composition)

| Component | (%) |
|---|---|
| (1) Talc | 49.8 |
| (2) Magnesium stearate | 5.0 |
| (3) Hydroxyapatite powder (10%) covered spherical nylon* | 45.0 |
| (4) Perfume | 0.1 |
| (5) Bactericide | 0.1 |

*In the same way as in Example 1, 90 parts of spherical nylon powder (average particle size 5 microns) were mixed with 10 parts of hydroxyapatite powder (average particle size 0.1 micron) in a Henschel mixer for 5 minutes, then the obtained mixed powder was mixed and compressed in a vibration ball mill charged with alumina balls (2 mmϕ) for 6 hours.

Production Process

Components (1) to (3) and (5) were mixed well with a blender while component (4) was sprayed thereon. The mixture was shaped into a shallow dish to give a solid powder form skin treatment agent.

COMPARATIVE EXAMPLE 5

(Composition)

| Component | (%) |
|---|---|
| (1) Talc | 49.8 |

-continued

| (Composition) | |
|---|---|
| Component | (%) |
| (2) Magnesium stearate | 5.0 |
| (3) Hydroxyapatite powder | 4.5 |
| (4) Spherical nylon | 40.5 |
| (5) Perfume | 0.1 |
| (6) Bactericide | 0.1 |

CONFIRMATION OF EFFECTS BY TEST USE

Twenty test subjects suffering from rough skin used the powder skin treatment agent obtained in Example 15 and the agent of Comparative Example 5, in which the hydroxyapatite was not combined to make a composite powder but merely added therein, on their faces for a period of three months and the effects on the prevention of rough skin observed. The results are shown in Table 2. Compared with Comparative Example 2, with the agent of Example 15, a large number of the test subjects, 30 percent, stated that there had been a clear improvement in their rough skin or some improvement in their rough skin, thus indicating that the composite powder of hydroxyapatite was more effective against rough skin.

TABLE 2

| | Ex. 15 | C. Ex. 5 |
|---|---|---|
| Clear improvement in rough skin | 8 subj. | 3 subj. |
| Some improvement in rough skin | 10 | 9 |
| No effect on rough skin | 2 | 8 |

EXAMPLE 16 Powder Form Skin Treatment (Composition)

| (Composition) | |
|---|---|
| Component | (%) |
| (1) Talc | 49.5 |
| (2) Hydroxyapatite powder (25%) covered spherical polyethylene* | 50.0 |
| (3) Perfume | 0.05 |

*A 75 part amount of spherical polyethylene powder (average particle size 10 microns) was mixed with 25 parts of hydroxyapatite powder (average particle size 0.2 micron) in a Henschel mixer for 5 minutes, then the obtained mixed powder was mixed and compressed in a tumbling mill charged with alumina balls (3 mmφ) for 6 hours.

Production Process

Components (1) to (2) were mixed well with a blender while component (3) was sprayed uniformly thereon, thus giving a powder skin treatment agent.

COMPARATIVE EXAMPLE 6

| (Composition) | |
|---|---|
| Component | (%) |
| (1) Talc | 49.95 |
| (2) Hydroxyapatite powder | 12.5 |
| (3) Spherical polyethylene powder | 37.5 |
| (4) Perfume | 0.05 |
| (Production Process) Same as Example 16. | |

CONFIRMATION OF EFFECTS BY TEST USE

Ten test subjects suffering from acne used the powder skin treatment agent obtained in Example 16 and the agent of Comparative Example 6, in which the hydroxyapatite was not combined to make a composite powder but merely added therein, on their faces for a period of three months and the effects on the prevention of acne observed. The results are shown in Table 3. Compared with Comparative Example 6, with the agent of Example 16, a large number of the test subjects, 40 percent, stated that there had been a clear improvement in the inflammation or some improvement in the inflammation, thus indicating that the composite powder alleviated inflammation induced by acne.

TABLE 3

| | Ex. 16 | C. Ex. 6 |
|---|---|---|
| Clear improvement in inflammation | 6 subj. | 3 subj. |
| Some improvement in inflammation | 3 | 2 |
| No effect | 1 | 5 |

EXAMPLE 17: OINTMENT

| (Composition) | |
|---|---|
| Component | (%) |
| (1) Ceresine | 20.0 |
| (2) Liquid paraffin | 18.0 |
| (3) POE (10 mol) monooleate ester* | 0.25 |
| (4) Glyceryl monostearate | 0.25 |
| (5) Vaseline | 35.0 |
| (6) Hydroxyapatite powder (10%) covered spherical nylon* | 5.0 |
| (7) Purified water | 17.5 |
| (8) Propylene glycol | 4.0 |

*See asterisked note of Example 15.

Production Process

Components (1) to (5) were mixed and melted at 70° C. (oil phase) and component (6) added thereto. Component (8) was melted into component (7) and the two held at 70° C. These were added to the oil phase. The mixture was emulsified uniformly with a homogenizing mixer, then cooled to give the ointment.

The ointment obtained in Example 17 featured superior effectiveness in the prevention of rough skin in actual use compared with an ointment wherein the hydroxyapatite was not combined to make a composite powder but merely added therein.

EXAMPLE 18: POWDER FOUNDATION

| (Composition) | |
|---|---|
| Component | (%) |
| (1) Sericite | 54.28 |
| (2) Talc | 20.0 |
| (3) Hydroxyapatite powder (33%) covered cellulose* | 3.0 |
| (4) Titanium dioxide | 6.5 |
| (5) Iron oxide | 3.5 |
| (6) Trimethylolpropane triisostearate | 5.0 |
| (7) Squalane | 6.0 |
| (8) Sorbitan sesquioleate | 1.0 |
| (9) Preservative | 0.5 |
| (10) Antioxidant | 0.02 |
| (11) Perfume | 0.2 |

*A 67 part amount of spherical cellulose powder (average particle size 25 microns) was mixed with 3 parts of hydroxyapatite powder (average particle size 1.2 micron) and processed by the same method as in the asterisked note of Example 16.

PRODUCTION PROCESS

Components (1) to (5) were mixed with a Henschel mixer. To this was added a mixture of components (6) to (11) which had been heated and melted together. This was mixed and pulverized, and then shaped into a shallow dish to give the powder foundation.

EXAMPLE 19: SOLID WHITE POWDER

| (Composition) | |
|---|---|
| Component | (%) |
| (1) Talc | 87.9 |
| (2) Hydroxyapatite powder (7%) covered spherical silica* | 10.0 |
| (3) Liquid paraffin | 2.0 |
| (4) Perfume | 0.1 |

*A 93 part amount of spherical silica powder (average particle size 1 micron) was mixed with 7 parts of hydroxyapatite powder (average particle size 0.05 micron) and processed by the same method as in the asterisked note of Example 15.

Production Process

Components (1) and (2) were mixed well with a blender while component (3) was uniformly sprayed thereon. This was shaped into a shallow dish to give a solid white powder.

EXAMPLE 20: Baby Powder

| (Composition) | |
|---|---|
| Component | (%) |
| (1) Talc | 80.0 |
| (2) Calcium carbonate | 17.0 |
| (3) Starch | 0.5 |
| (4) Hydroxyapatite powder (12%) covered spherical titanium dioxide* | 2.0 |
| (5) Bactericide | 0.3 |
| (6) Preservative | 0.2 |

*An 88 part amount of spherical titanium dioxide powder (average particle size 1 micron) was mixed with 12 parts of hydroxyapatite powder (average particle size 0.1 micron) and processed by the same method as in the asterisked note of Example 15.

Production Process

Components (1) to (6) were mixed well with a blender to give the baby powder.

EXAMPLE 21: Pack

| (Composition) | |
|---|---|
| Component | (%) |
| (1) Polyvinyl alcohol | 15.0 |
| (2) Polyethylene glycol | 3.0 |
| (3) Propylene glycol | 7.0 |
| (4) Ethanol | 10.0 |
| (5) Hydroxyapatite powder (7%) covered spherical silica* | 10.0 |
| (6) Methylparaben | 0.05 |
| (7) Perfume | 0.15 |
| (8) Purified water | 54.8 |

*See asterisked note of Example 19.

Production Process

Components (2), (3), and (6) were added to component (8) and dissolved therein. Next, component (1) was added, then the mixture heated and stirred for dissolution, then component (5) dispersed therein. Tho this was added components (4) and (7), the mixture was stirred for dissolution, and a pack was formed.

EXAMPLE 22: Cream

| (Composition) | |
|---|---|
| Component | (%) |
| (1) Cetostearyl alcohol | 3.5 |
| (2) Squalane | 20.0 |
| (3) Beeswax | 3.0 |
| (4) Lanolin | 5.0 |
| (5) Ethylparaben | 0.3 |
| (6) POE (20 mol) sorbitan monoleate ester* | 2.0 |
| (7) Glyceryl monostearate | 2.0 |
| (8) Hydroxyapatite powder (33%) covered spherical cellulose* | 5.0 |
| (9) Perfume | 0.1 |
| (10) 1,3-butylene glycol | 5.0 |
| (11) Glycerine | 5.0 |
| (12) Purified water | 49.1 |

*See asterisked note of Example 18.

Production Process

Components (1) to (b 7) and (9) were heated to melting point and maintained at 75° C. (oil phase). Components (10) and (11) were dissolved in component (12), then component (8) added and dispersed therein and the mixture heated to 75° C. (water phase). The oil phase was added to the water phase, then the two were emulsified by a homogenizer and cooled to form the cream.

The cosmetics obtained in Examples 18 to 22, compared with cosmetic wherein, instead of adding the hydroxyapatite composite powders of the examples, use was made of another, noncomposite powder, feature a good feel during application in actual use and a uniform spreadability, and further, help maintain skin smoothness and are effective against skin roughness.

EXAMPLE 23: SUNBURN PREVENTING FACIAL FOUNDATION

| (Composition) | |
|---|---|
| Component | (%) |
| (1) 15% zinc oxide covered nylon powder* | 20.0 |
| (2) Silicone treated mica | 40.0 |
| (3) Silicone treated talc | 20.45 |
| (4) Silicone treated iron oxide | 7.5 |
| (5) Trimethylolpropane triisostearate | 5.0 |
| (6) Squalane | 3.0 |
| (7) Beeswax | 2.0 |
| (8) Sorbitan trioleate | 1.0 |
| (9) Propylparaben | 0.5 |
| (10) Vitamin E | 0.05 |
| (11) Perfume | 0.5 |

*Here, 150 g of zinc oxide (average particle size 0.05 microns) and 850 g of spherical nylon powder (average particle size 5 microns) were charged into a 5 liter capacity tumbling mill and treated for 3 hours. The obtained powder was observed by electron microscope, whereby it was found that the nylon powder was completely covered by the 15% zinc oxide.

Production Process

Components (1) to (4) were mixed in a Henschel mixer. To this was added and mixed a mixture of components (5) to (11) heated and melted together. This was then pulverized and shaped into a shallow dish form to give a sunburn preventing facial foundation.

The foundation of Example 23 was easy to apply and gave a natural finish.

COMPARATIVE EXAMPLE 7: SUNBURN PREVENTION FACIAL FOUNDATION

In the composition of Example 23, component (1) was omitted and 3 percent zinc oxide and 17 percent nylon powder were compounded without covering treatment. Otherwise, the sunburn preventing facial foundation was obtained in the same way as in Example 23.

The foundation of Comparative Example 6 was difficult to apply and did not give a satisfactory feeling during use.

EXAMPLE 24: SUNBURN PREVENTING CREAM

| Example 24: Sunburn Preventing Cream (Composition) | |
|---|---|
| Component | (%) |
| (1) 40% zinc oxide covered polyethylene* | 5.0 |
| (2) Cetanol | 5.0 |
| (3) Stearic acid | 3.0 |
| (4) Vaseline | 5.0 |
| (5) Squalane | 2.0 |
| (6) Isopropylmyristate | 2.0 |
| (7) Liquid paraffin | 5.0 |
| (8) Glyceryl monoisostearate | 3.0 |
| (9) Ethylparaben | 0.2 |
| (10) Perfume | 0.2 |
| (11) Glycerine | 10.0 |
| (12) Propylene glycol | 5.0 |
| (13) Hyaluronic acid | 0.01 |
| (14) Potassium hydroxide | 0.2 |
| (15) Purified water | 54.39 |

*Here, 400 g of zinc oxide (average particle size 0.1 micron) and 600 g of polyethylene powder (average particle size 10 microns) were charged into a 5 liter capacity vibration ball mill and treated for 1 hour.

The obtained powder was observed by an electron microscope, whereby it was found that the polyethylene powder was completely covered by the 40 percent zinc oxide.

Production Process

Components (1) to (10) were heated and stirred to form the oil phase. Components (11) to (15) were mixed and heated to 70° C. to ensure complete dissolution to form the water phase. The oil phase was mixed in the water phase and an emulsion formed by an emulsifier. The emulsion was cooled by a heat exchanger to 30° C., then filled in a container to give the sunburn preventing cream.

COMPARATIVE EXAMPLE 8: SUNBURN PREVENTING CREAM

In the composition of Example 24, component (1) was omitted and 2 percent zinc oxide and 3 percent polyethylene powder were compounded without covering treatment. Otherwise, the sunburn preventing cream was obtained in the same way as in Example 24.

EXAMPLE 25: SUNBURN PREVENTING LOTION

| Example 25: Sunburn Preventing Lotion (Composition) | |
|---|---|
| Component | (%) |
| (1) 30% zinc oxide covered polymethyl metacrylate resin | 7.0 |
| (2) Stearic acid | 1.0 |
| (3) Dimethylpolysiloxane (5CS/25° C.) | 10.0 |
| (4) Glycerylmonoisostearate | 1.5 |
| (5) Ethylparaben | 0.2 |
| (6) Butylparaben | 0.2 |
| (7) Perfume | 0.15 |
| (8) Glycerine | 5.0 |
| (9) Montmorillonite | 0.5 |
| (10) Potassium hydroxide | 0.2 |
| (11) Purified water | 74.25 |

Production Process

Components (1) to (7) were heated and stirred to form the oil phase. Components (8) to (11) were mixed and heated to 70° C. to ensure complete dissolution to form the water phase. The oil phase was mixed in the water phase and an emulsion formed by an emulsifier. The emulsion was cooled by a heat exchanger to 30° C., then filled in a container to give the sunburn preventing lotion.

COMPARATIVE EXAMPLE 9: SUNBURN PREVENTION LOTION

In the composition of Example 25, component (1) was omitted and 2.1 percent zinc oxide and 4.9 percent polymethyl metacrylate were compounded without covering treatment. Otherwise, the sunburn preventing lotion was obtained in the same way as in Example 25.

EXAMPLE 26: SUNBURN PREVENTING POWDER FOUNDATION

| Example 26: Sunburn Preventing Powder Foundation (Composition) | |
|---|---|
| Component | (%) |
| (1) 10% zinc oxide covered nylon powder | 16.0 |
| (2) Talc | 20.8 |
| (3) Muscovite | 50.0 |
| (4) Red iron oxide | 1.0 |
| (5) Yellow iron oxide | 0.7 |
| (6) Black iron oxide | 0.1 |
| (7) Dimethylpolysiloxane (5CS/25° C.) | 1.0 |
| (8) Cetyl 2-ethylhexanoate | 9.0 |
| (9) Sorbitan sesquioleate | 1.0 |
| (10) Propylparaben | 0.3 |
| (11) Perfume | 0.1 |

Production Process

Components (1) to (6) were mixed in a Henschel mixer. To this was added and mixed a mixture of components (7) to (11) heated and melted together. This was then pulverized and shaped into a shallow dish form to give a sunburn preventing powder foundation.

COMPARATIVE EXAMPLE 10: SUNBURN PREVENTING POWDER FOUNDATION

In the composition of Example 26, component (1) was omitted and 1.6 percent zinc oxide and 14.4 percent nylon powder were compounded without covering treatment. Otherwise, the sunburn preventing powder foundation was obtained in the same way as in Example 26.

The products of Examples 23 to 26 and Comparative Examples 6 to 9, obtained as explained above, were measured for effectiveness in blocking ultraviolet rays.

The effectiveness in blocking ultraviolet rays was determined using the ultraviolet sensitive composition shown below:

| Formulation of Ultraviolet Sensitive Composition (Japanese Patent Application No. 60-250678) | |
| --- | --- |
| Solution I | |
| Leukocrystal violet | 1.0 g |
| Tetrabromodimethylsulfone | 0.1 g |
| Ethylene-vinyl acetate copolymer | 10 g |
| Toluene | 100 ml |
| Solution II | |
| N,N-dimethylparaaminobenzoate 2-ethylhexylester | 7 g |
| Ethylene-vinyl acetate copolymer | 10 g |
| Toluene | 100 ml |

Solutions I and II were separately prepared. First, solution I was applied on photographic paper in a thickness of 1 g/m² solids content, then solution II was applied on the top for a thickness of 5 g/m² solids content.

The ultraviolet sensitive composition was irradiated by ultraviolet light. In accordance with the increase in the amount of ultraviolet light irradiated, the paper changed color from white to light purple, to purple, and to dark purple. A 40 mg amount of the sample to be measured was mixed in 12 g of castor oil, then a roller treatment applied for an even dispersion. Transparent PET film was placed on the above-mentioned ultraviolet sensitive composition, formed in a cylindrical shape with a diameter of 5 cm. To this, 1.5 g of the sample was applied in an even thickness. An ultraviolet lamp was turned on for 8 minutes. The PET film was removed with each sample and the color-forming ultraviolet sensitive composition was measured using a Hitachi 607 spectrophotometer to calculate the color difference with an LAB coordinate system, based on the color of the ultraviolet sensitive composition under zero ultraviolet irradiation.

The results are shown in Table 4.

TABLE 4

| | Color difference |
| --- | --- |
| Example 23 | 28 |
| Comparative Example 6 | 39 |
| Example 24 | 36 |
| Comparative Example 7 | 45 |
| Example 25 | 41 |
| Comparative Example 8 | 57 |
| Example 26 | 29 |
| Comparative Example 9 | 39 |

As understood from Table 4, the color differences of the examples were smaller than those of the corresponding comparative examples, indicating a higher effectiveness in blocking ultraviolet rays. That is, by depositing zinc oxide uniformly on the surface of a resin powder, it is possible to raise the effectiveness in scattering ultraviolet rays.

EXAMPLE 27: SUNBURN PREVENTING LOOSE POWDER

| Example 27: Sunburn Preventing Loose Powder (Composition) | |
| --- | --- |
| Component | (%) |
| (1) 60% zinc oxide covered polystyrene powder | 55.0 |
| (2) Talc | 10.0 |
| (3) Mica | 29.5 |
| (4) Red iron oxide | 2.0 |
| (5) Yellow iron oxide | 2.0 |
| (6) Black iron oxide | 1.0 |
| (7) Perfume | 0.5 |

Components (1) to (7) were mixed in a Henschel mixer to obtain the sunburn preventing loose powder.

The product of Example 27 had a smooth feeling during use and was highly effective in blocking out ultraviolet light.

EXAMPLE 28: SUNBURN PREVENTING STICK COSMETIC

| Example 28: Sunburn Preventing Stick Cosmetic (Composition) | |
| --- | --- |
| Component | (%) |
| (1) 5% zinc oxide/3% silicic acid anhydride covered teflon powder | 10.0 |
| (2) Titanium oxide | 10.0 |
| (3) Mica | 16.0 |
| (4) Red iron oxide | 1.5 |
| (5) Yellow iron oxide | 1.5 |
| (6) Black iron oxide | 1.0 |
| (7) Squalane | 39.4 |
| (8) Trimethylolpropane tri-2-ethylhexanoate | 10.0 |
| (9) Solid paraffin | 6.0 |
| (10) Microcrystalline wax | 2.0 |
| (11) Ceresine | 1.0 |
| (12) Perfume | 0.5 |
| (13) Antioxidant | 0.1 |
| (14) Sorbitan sesquiolate | 1.0 |

Production Process

Components (1) to (6) were mixed together, and then added to components (7), (8), (13), and (14), which were heated and stirred, then the mixture further mixed and pulverized. Next, a molten mixture of components (9), (10), (11), and (12) was added to the above mixture. This was fully mixed, then shaped into a stick form to give the sunburn preventing stick cosmetic.

The product of Example 28 had a good ultraviolet blocking effect and had a superior cosmetic effect due to the skin oil fixing action of the zinc oxide and the sweat absorption action of the anhydrous silicic acid.

EXAMPLE 29: DEODORANT POWDER

Composition

A 40 g amount of hydroxyapatite powder (specific surface area 70.4 m²/g, Sumitomo Chemical) and 50 g of nylon (Nylon 12 spherical, average particle size 5 microns, Nylon SP-500, Nikko Rikagaku Sangyo) were mixed using a Mitsui Mike Machinery Co., Model FM1-B Henschel mixer for 10 minutes to homogenize them and obtain the composite powder. Next, the composite powder was used to form a deodorant powder having the following composition.

| Component | (%) |
| --- | --- |
| Composite powder | 40.0 |
| Talc | 60.0 |

Using the above powder, a deodorizing test was conducted by the following method, whereupon it was found that, after the start of the test, in the case of all subjects on the test panel, the underarm odor intensity of the test portion was 5 percent in terms of risk compared with the control portion; which was significantly lower.

Deodorizing Test Method

A panel of six healthy men believing themselves to suffer from underarm odor was used for testing the deodorant containing the composite powder of the present invention. The test product was applied directly to the test underarm a total of four times: once in the morning and once in the afternoon for two days. The untested underarm was used as the control portion.

The judgment was made using the following five stages:
- 0: No underarm odor
- 1: Some underarm odor
- 2: Clear underarm odor
- 3: Strong underarm odor
- 4: Very strong underarm odor

EXAMPLE 30: AEROSOL DEODORANT SPRAY

A 70 ml amount of sintered alumina balls of an average size of 2 mm$\phi$, 20 g of hydroxyapatite (specific surface area 70.4 m$^2$/g), and 80 g of nylon (average particle size 5 microns) were filled into a centrifugal tumbling mill and subjected to ball milling for 30 minutes.

Using the resultant composite powder, an aerosol deodorant spray having the following composition was prepared.

| Component | (%) |
|---|---|
| Freon 11 | 76.8 |
| Freon 12 | 19.2 |
| Composite powder | 1.5 |
| Talc | 1.5 |
| Isopropyl myristate | 0.5 |
| Diglyceryl tetra-2-ethylhexanoate | 0.5 |

Figure 5:
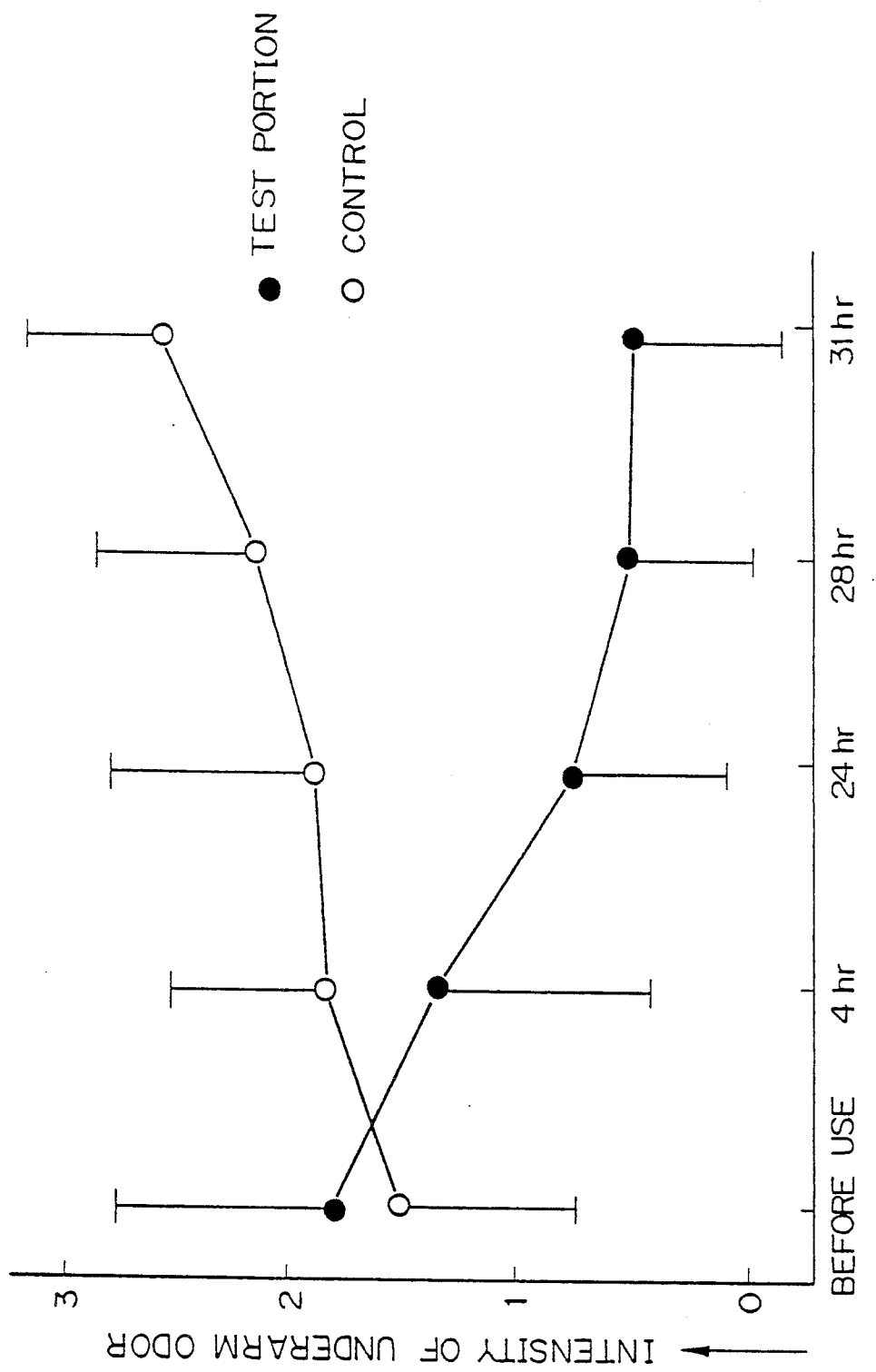
FIG. 5 shows the effects of an aerosol type deodorant spray in Example 30.

In actual test use of this spray, even after the start of the test, as shown in FIG. 5, the intensity of underarm odor of the test portions of all test subjects on the panel was 5 percent in terms of risk; significantly lower than the control portions.

Figure 6:
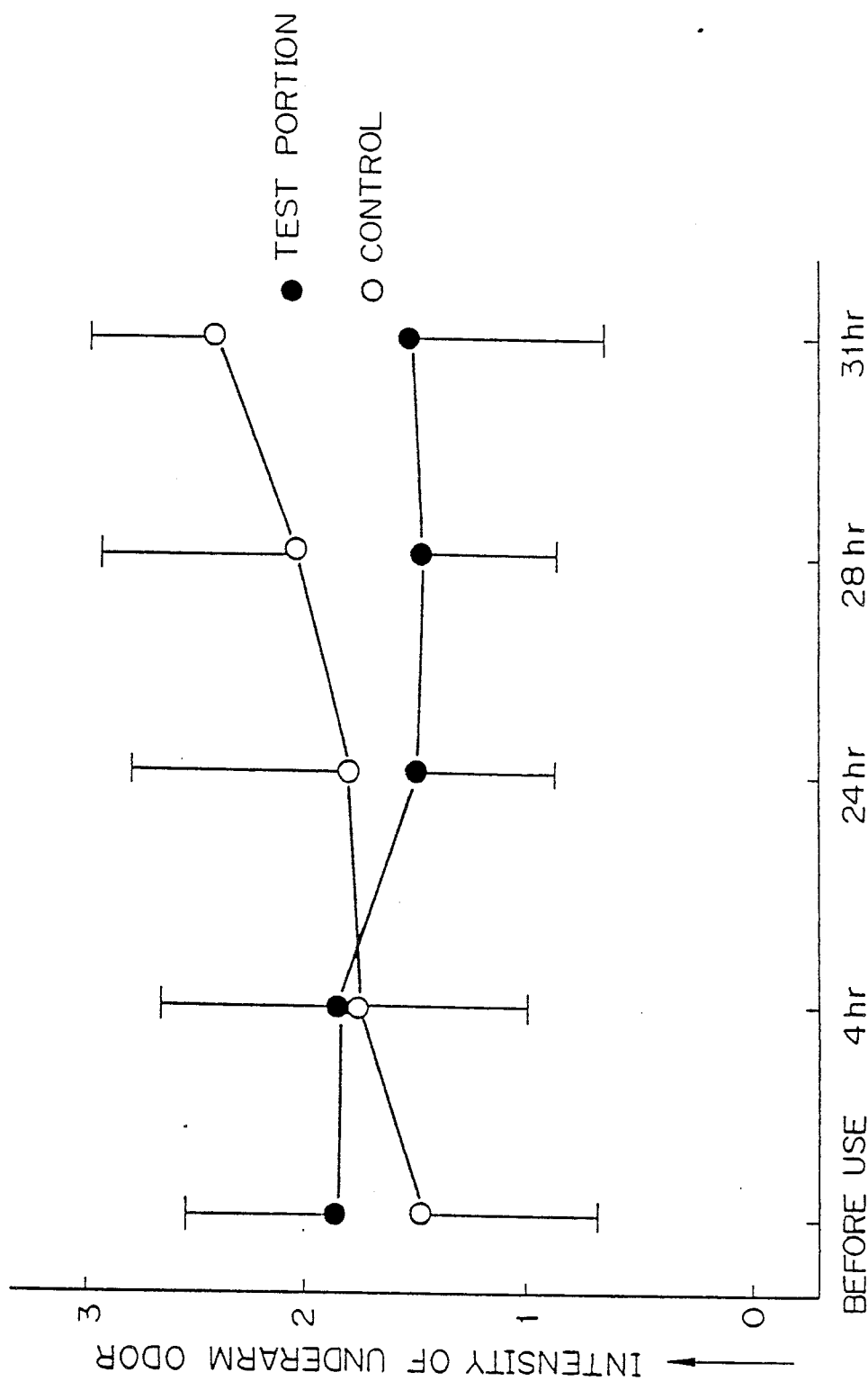
FIG. 6 is a graph showing the changes with time in the strength of the underarm odor of a test portion and control portion in an actual usage test employing an aerosol deodorant spray wherein the composite powder in the deodorant spray of Example 30 is replaced with nylon.
Figure 7:
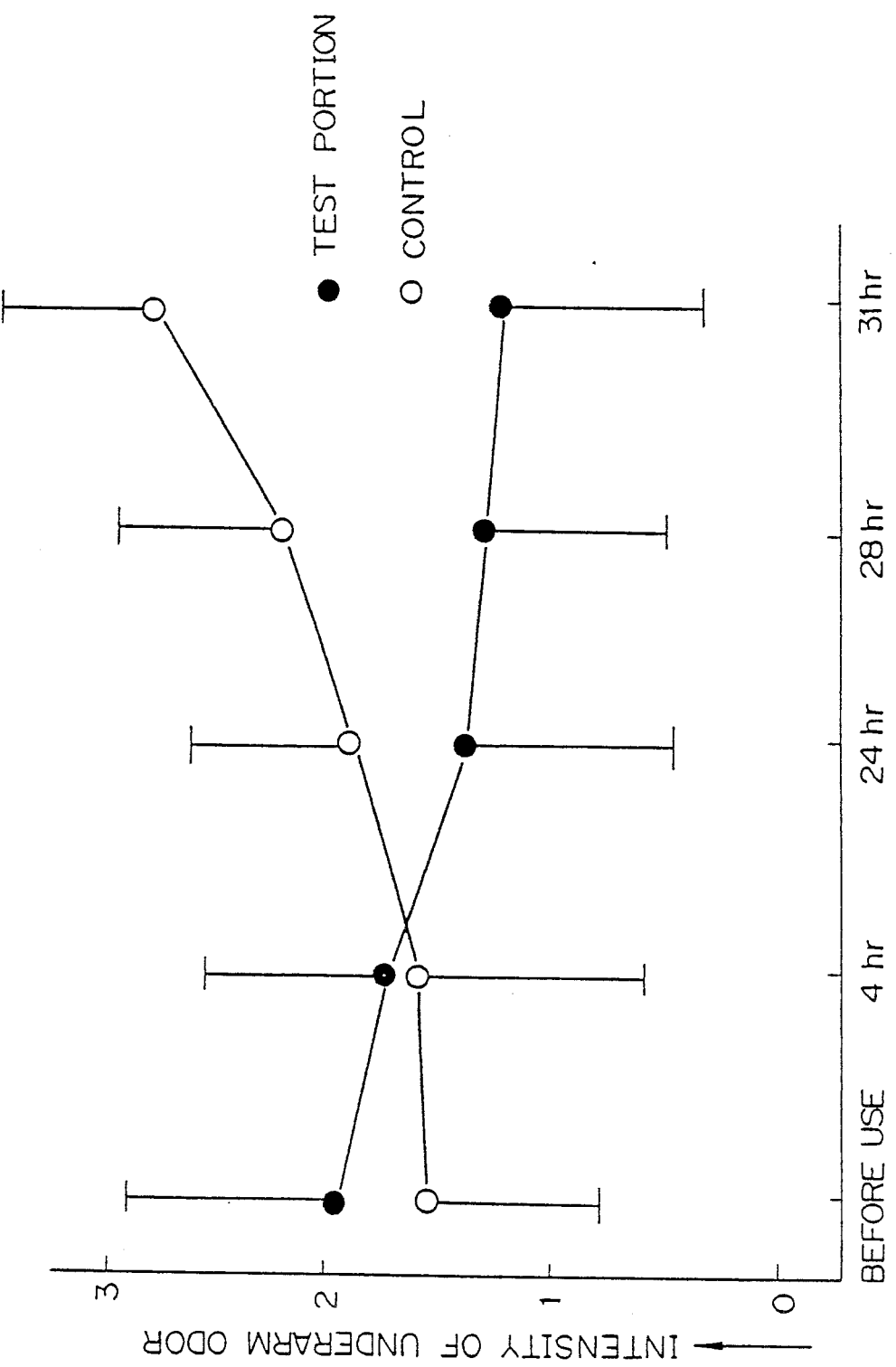
FIG. 7 is a graph showing the changes with time in the strength of the underarm odor with a deodorant spray of Example 30 wherein the composite powder is replaced with zinc oxide.

FIGS. 6 and 7 show the changes over time of the underarm odor intensity in the case of the aerosol deodorant spray of Example 30 in which the composite powder was replaced with nylon and hydroxyapatite powder. The change over time of the underarm odor intensity in the case of the aerosol deodorant spray of Example 30, on the other hand, is shown in FIG. 5.

EXAMPLE 31: AEROSOL DEODORANT SPRAY

In the same way as in Example 30, 40 g of hydroxyapatite and 60 g of nylon were ball milled. Using the obtained composite powder, an aerosol deodorant spray having the following composition was prepared.

| Component | (%) |
|---|---|
| Freon 11 | 76.8 |
| Freon 12 | 19.2 |
| Composite powder | 1.0 |
| Talc | 2.0 |
| Isopropyl myristate | 0.5 |
| Diglyceryl tetra-2-ethylhexanoate | 0.5 |

At the start of the actual test use of this spray, after the start of the test, the intensity of underarm odor of the test portions of all test subjects on the panel was 5 percent in terms of risk; significantly lower than the control portions.

EXAMPLE 32: DEODORANT POWDER

In the same way as in Example 30, 30 g of hydroxyapatite and 70 g of nylon were ball milled. Using the obtained composite powder, a deodorant powder having the following composition was prepared.

| Component | (%) |
|---|---|
| Composite powder | 50.0 |
| Talc | 50.0 |

Upon actual test use of the deodorant powder, it was found that, after the start of the test, the intensity of underarm odor of the test portions of all test subjects on the panel was 5 percent in terms of risk; significantly lower than the control portions.

EXAMPLE 33: DEODORANT POWDER

In the same way as in Example 30, 20 g of hydroxyapatite and 80 g of nylon were ball milled. Using the obtained composite powder, a deodorant powder having the following composition was prepared.

| Component | (%) |
|---|---|
| Composite powder | 30.0 |
| Talc | 70.0 |

Along with use of the deodorant powder, the intensity of underarm odor of all test subjects on the panel decreased with time, proving the effectiveness of the powder.

EXAMPLE, 34: DEODORANT POWDER

Composition

A 50 g amount of zinc oxide (#1 special grade, average particle size 0.5 microns, Sakai Kagaku) and 50 g of nylon (Nylon 12 spherical, average particle size 5 microns, Nylon SP-500, Nikko Rikagaku Sangyo) were mixed using a Mitsui Miike Machinery Co., Model FM1-B Henschel mixer for 10 minutes to homogenize them and obtain the composite powder. Next, the composite powder was used to form a deodorant powder having the following composition.

| Component | (%) |
|---|---|
| Composite powder | 50.0 |
| Talc | 50.0 |

Using the above powder, a deodorizing test was conducted by the same method as in Example 29, whereupon it was found that, after the start of the test, in the case of all subjects on the test panel, the underarm odor intensity of the test portion was 5 percent in terms of risk compared with the control portion; which was significantly lower.

EXAMPLE 35: AEROSOL DEODORANT SPRAY

A 70 ml amount of sintered alumina balls of an average size of 2 mm$\phi$, 20 g of zinc oxide (average particle size 20 microns), and 80 g of nylon (average particle size 5 microns) were filled into a centrifugal tumbling mill and subjected to ball milling for 30 minutes.

Using the resultant composite powder, an aerosol deodorant spray having the following composition was prepared.

| Component | (%) |
|---|---|
| Freon 11 | 76.8 |
| Freon 12 | 19.2 |
| Composite powder | 1.5 |
| Talc | 1.5 |
| Isopropyl myristate | 0.5 |
| Diglyceryl tetra-2-ethylhexanoate | 0.5 |

In actual test use of this spray as in Example 29, even after the start of the test, the intensity of underarm odor of the test portions of all test subjects on the panel was 5 percent in terms of risk; significantly lower than the control portions.

EXAMPLE 36: AEROSOL DEODORANT SPRAY

In the same way as in Example 35, 40 g of zinc oxide and 60 g of nylon were ball milled. Using the obtained composite powder, an aerosol deodorant spray having the following composition was prepared.

| Component | (%) |
|---|---|
| Freon 11 | 76.8 |
| Freon 12 | 19.2 |
| Composite powder | 0.6 |
| Talc | 2.4 |
| Isopropyl myristate | 0.5 |
| Diglyceryl tetra-2-ethylhexanoate | 0.5 |

At the start of actual test use of this spray, after the start of the test, the intensity of underarm odor of the test portions of all test subjects on the panel was 5 percent in terms of risk; significantly lower than the control portions.

EXAMPLE 37: DEODORANT POWDER

In the same way as in Example 35, 30 g of zinc oxide and 70 g of nylon were ball milled. Using the obtained composite powder, a deodorant powder having the following composition was prepared.

| Component | (%) |
|---|---|
| Composite powder | 50.0 |
| Talc | 50.0 |

Upon actual test use of the deodorant powder, it was found that, after the start of the test, the intensity of underarm odor of the test portions of all test subjects on the panel was 5 percent in terms of risk; significantly lower than the control portions.

EXAMPLE 38: DEODORANT POWDER

In the same way as in Example 35, 20 g of zinc oxide and 80 g of nylon were ball milled. Using the obtained composite powder, a deodorant powder having the following composition was prepared.

| Component | (%) |
|---|---|
| Composite powder | 30.0 |
| Talc | 70.0 |

Along with use of the deodorant powder, the intensity of underarm odor of all test subjects on the panel decreased along with time, proving the effectiveness.

EXAMPLE 39: DEODORANT POWDER

Composition

A 50 g amount of aluminum hydroxychloride and 50 g of nylon (Nylon 12 spherical, average particle size 5 microns, Nylon SP-500, Nikko Rikagaku Sangyo) were mixed using a Mitsui Miike Machinery Co., Model FM1-B Henschel mixer for 10 minutes to homogenize them and obtain the composite powder. Next, the composite powder was used to form a deodorant powder having the following composition.

| Component | (%) |
|---|---|
| Composite powder | 0.1 |
| Talc | 79.9 |
| Kaolin | 20.0 |

Using the above powder, a deodorizing test was conducted by the same method as in Example 29, whereupon it was found that, after the start of the test, in the case of all subjects on the test panel, the underarm odor intensity of the test portion was 5 percent in terms of risk compared with the control portion; which was significantly lower.

EXAMPLE 40: DEODORANT POWDER

Composition

A 50 g amount of benzalkonium chloride and 50 g of polyethylene (average particle size 5 microns) were mixed using a Mitsui Miike Machinery Co., Model FM1-B Henschel mixer for 10 minutes to homogenize them and obtain the composite powder. Next, the composite powder was used to form a deodorant powder having the following composition.

| Component | (%) |
|---|---|
| Composite powder | 5.0 |
| Talc | 85.0 |
| Kaolin | 10.0 |

Using the above powder, a deodorizing test was conducted by the same method as in Example 29, whereupon it was found that, after the start of the test, in the case of all subjects on the test panel, the underarm odor intensity of the test portion was 5 percent in terms of risk compared with the control portion; which was significantly lower.

EXAMPLE 41: AEROSOL DEODORANT SPRAY

Using the same composite powder as in Example 39, an aerosol deodorant spray having the following composition was prepared.

| Component | (%) |
|---|---|
| Freon 11 | 76.8 |
| Freon 12 | 19.2 |
| Composite powder | 0.6 |
| Talc | 2.4 |
| Isopropyl myristate | 0.5 |
| Diglyceryl tetra-2-ethylhexanoate | 0.5 |

In actual test use of this spray, even after the start of the test, the intensity of underarm odor of the test portions of all test subjects on the panel was 5 percent in terms of risk; significantly lower than the control portions.

EXAMPLE 42: DEODORANT LOTION

A deodorant lotion having the following composition was prepared.

| Component | (%) |
|---|---|
| Purified water | 82.0 |
| Ethanol | 15.0 |
| Sorbitol | 2.0 |
| Composite powder (the same as in Example 39) | 1.0 |

In actual use test of this lotion, even after the start of the test, the intensity of underarm odor of the test portions of all test subjects on the panel was 5 percent in the terms of risk; significantly lower than the control portions.

We claim:

1. A composite powder comprising a core powder having an average particle size of 0.5 to 100 μm substantially completely covered with a coating powder having an average particle size of one-fifth or less of the average particle size of the above-mentioned core powder, said core powder being at least one powder selected from the group consisting of polyamide resin, polyethylene resin, acrylic resin, polyester resin, fluorine resin and cellulose resin, and said coating powder being at least one coating powder selected from the group consisting of titanium dioxide, talc, kaolisite, zinc white, magnesium oxide, calcium oxide, barium sulfate, magnesium carbonate, calcium carbonate, silica, calcium secondary phosphate, iron oxide, chromium oxide, chromium hydroxide, ultramarine blue, prussian blue, hydroxyapatite, and silicon treated, activant treated and wax treated powder thereof, aluminum gold, silver, and iron powder and the halogen compounds thereof, said composite powder being produced by dry mixing and dry compressing the organic or inorganic powder constituting the core powder and one or more types of the organic, inorganic, or metallic powders constituting the coating powder, a mixer charged with a ball shaped mixing medium having an average diameter of at most 5 m being used to produce the composite powder.

2. A skin treatment agent comprising a spherical composite powder produced by dry mixing and dry compressing an organic or inorganic spherical core powder and hydroxyapatite coating powder, so that the spherical core powder having an average particle size of 0.5 to 100 microns is substantially completely covered by the coating powder having an average particle size of one-fifth or less of the average particle size of the above core powder, a mixer charged with a ball shaped mixing medium having an average diameter of at most 5 mm being used to produce the composite powder, said core powder being at least one powder selected from the group consisting of polyamide resin, polyethylene resin, acrylic resin, polyester resin, fluorine resin and cellulose resin, and said coating powder at least one coating powder selected from the group consisting of titanium dioxide, talc, kaolisite, zinc white, magnesium oxide, calcium oxide, barium sulfate, magnesium carbonate, calcium carbonate, silica, calcium secondary phosphate, iron oxide, chromium oxide, chromium hydroxide, ultramarine blue, prussian blue, hydroxyapatite, and silicon treated, activant treated and wax treated powder thereof, aluminum gold, silver, and iron powder and the halogen compounds thereof.

3. A makeup type cosmetic comprising a spherical composite powder produced by dry mixing and dry compressing a spherical core powder and a coating powder so as to substantially completely cover the spherical core powder having an average particle size of 0.5 to 100 μm with the coating powder having an average particle size of one-fifth or less of the average particle size of the above-mentioned core powder, a mixer charged with a ball shaped mixing medium having an average diameter of at most 5 mm being used to produce the composite powder, said core powder being at least one powder selected from the group consisting of polyamide resin, polyethylene resin, acrylic resin, polyester resin, fluorine resin and cellulose resin, and said coating powder at least one coating powder selected from the group consisting of titanium dioxide, talc, kaolisite, zinc white, magnesium oxide, calcium oxide, barium sulfate, magnesium carbonate, calcium carbonate, silica, calcium secondary phosphate, iron oxide, chromium oxide, chromium hydroxide, ultramarine blue, prussian blue, hydroxyapatite, and silicon treated, activant treated and wax treated powder thereof, aluminum gold, silver, and iron powder and the halogen compounds thereof.

4. A composite powder wherein a polyethylene core powder having an average particle size of 0.5 to 100 μm is substantially completely covered with a coating powder composed of silica having an average particle size of one-fifth or less of the average particle size of the above-mentioned core powder, said composite powder being produced by dry mixing and dry compressing said composite.

5. A process for the production of a composite powder comprising dry mixing and dry compressing a polyethylene core powder and silica, wherein a mixer charged with a ball shaped mixing medium having an average diameter of 0.5 μm or less is used to produce a composite in which said core powder having an average particle size of 0.5 to 100 μm is substantially completely covered by said silica having an average particle size of one-fifth or less of said polyethylene core powder.

* * * * *

UNITED STATES PATENT AND TRADEMARK OFFICE
CERTIFICATE OF CORRECTION

PATENT NO. : 5,122,418
DATED : June 16, 1992
INVENTOR(S) : Nakane et al.

It is certified that error appears in the above-identified patent and that said Letters Patent is hereby corrected as shown below:

Col. 33, lines 48-49    Delete " 5m " and substitute -- 5mm --

Col. 34, line 16        Delete " type "

Col. 34, line 52        Delete " 0.5 " and substitute -- 5 --

Signed and Sealed this

Twenty-second Day of March, 1994

Attest:

BRUCE LEHMAN

Attesting Officer    Commissioner of Patents and Trademarks